US008083408B2

(12) United States Patent
Moyers

(10) Patent No.: US 8,083,408 B2
(45) Date of Patent: Dec. 27, 2011

(54) METHOD AND DEVICE FOR DELIVERING RADIOTHERAPY

(75) Inventor: Michael F. Moyers, Colton, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 0 days.

(21) Appl. No.: 12/877,019

(22) Filed: Sep. 7, 2010

(65) Prior Publication Data
US 2011/0057122 A1 Mar. 10, 2011

Related U.S. Application Data

(63) Continuation of application No. 12/033,843, filed on Feb. 19, 2008, now Pat. No. 7,789,560, which is a continuation of application No. 11/314,138, filed on Dec. 21, 2005, now Pat. No. 7,331,713, which is a continuation of application No. 10/887,507, filed on Jul. 7, 2004, now Pat. No. 7,011,447, which is a continuation of application No. 10/393,836, filed on Mar. 20, 2003, now Pat. No. 6,769,806, which is a continuation of application No. PCT/US02/34556, filed on Oct. 28, 2002.

(60) Provisional application No. 60/340,430, filed on Oct. 30, 2001.

(51) Int. Cl.
*A61B 6/04* (2006.01)
(52) U.S. Cl. .......................................... 378/205; 378/65
(58) Field of Classification Search ................... 378/65, 378/204, 205, 208, 209
See application file for complete search history.

(56) References Cited

U.S. PATENT DOCUMENTS

| 2,469,084 | A | 5/1949 | Schenker |
| 2,675,564 | A | 4/1954 | Hughes |
| 3,397,411 | A | 8/1968 | Rossi |
| 3,449,570 | A | 6/1969 | Kok |
| 3,545,739 | A | 12/1970 | D'Avignon |
| 3,556,455 | A | 1/1971 | Storm |
| 3,604,931 | A | 9/1971 | Kastner et al. |

(Continued)

FOREIGN PATENT DOCUMENTS
DE          2513896        10/1975

(Continued)

OTHER PUBLICATIONS

"Dedicated Medical Ion Accelerator Design Study" by Lawrence Berkeley Laboratory, et al., Dec. 1977, PCTA008295-PCTA008455.

(Continued)

*Primary Examiner* — Courtney Thomas
(74) *Attorney, Agent, or Firm* — Knobbe, Martens, Olson & Bear, LLP

(57) ABSTRACT

A device 10 for aligning a patient for delivering a plurality of radiation beams comprising a patient support surface 12, a coarse alignment subsystem 14 connected to the patient support surface, and a fine alignment subsystem connected to the patient support surface 16. A method of aligning a patient for delivering a plurality of radiation beams from a plurality of device positions comprising compensating for flexion of a radiation beam delivery device within a gantry during movement of the radiation beam delivery device from a first device position to a second device position by using a set of predetermined data describing the flexion behavior of the radiation beam delivery device so that the target tissue within the patient is placed at the beamline center for the radiation beam delivery device at the second device position.

17 Claims, 19 Drawing Sheets

U.S. PATENT DOCUMENTS

| | | |
|---|---|---|
| 3,640,787 A | 2/1972 | Heller |
| 3,689,949 A | 9/1972 | Weinstein et al. |
| 3,745,998 A | 7/1973 | Rose |
| 3,762,404 A | 10/1973 | Sakita |
| 3,778,049 A | 12/1973 | Viamonte, Jr. |
| 3,848,132 A | 11/1974 | Foderaro |
| 3,851,644 A | 12/1974 | Slagle |
| 3,885,258 A | 5/1975 | Regan |
| 3,893,198 A | 7/1975 | Blair |
| 3,897,345 A | 7/1975 | Foster |
| 3,897,777 A | 8/1975 | Morrison |
| 3,901,588 A | 8/1975 | Longhenry |
| 3,905,054 A | 9/1975 | Windsor et al. |
| 3,947,686 A | 3/1976 | Cooper et al. |
| 3,986,697 A | 10/1976 | Amor, Jr. et al. |
| 4,034,224 A | 7/1977 | Heavens et al. |
| 4,064,401 A | 12/1977 | Marden |
| 4,190,772 A | 2/1980 | Dinwiddie et al. |
| 4,230,129 A | 10/1980 | LeVeen |
| 4,252,594 A | 2/1981 | Cooper |
| 4,256,112 A | 3/1981 | Kopf et al. |
| 4,262,204 A | 4/1981 | Mirabella |
| 4,269,512 A | 5/1981 | Nosler |
| 4,287,425 A | 9/1981 | Elliott, Jr. |
| 4,327,046 A | 4/1982 | Davis et al. |
| 4,347,213 A | 8/1982 | Rogers, Jr. |
| 4,365,341 A | 12/1982 | Lam |
| 4,392,239 A | 7/1983 | Wilkens |
| 4,400,820 A | 8/1983 | O'Dell et al. |
| 4,450,122 A | 5/1984 | Gallina |
| 4,484,571 A | 11/1984 | Velasquez |
| 4,504,050 A | 3/1985 | Osborne |
| 4,552,508 A | 11/1985 | Reid |
| 4,578,757 A | 3/1986 | Stark |
| 4,591,341 A | 5/1986 | Andrews |
| 4,616,814 A | 10/1986 | Harwood-Nash et al. |
| 4,666,304 A | 5/1987 | Davies |
| 4,671,284 A | 6/1987 | Wilson et al. |
| 4,682,818 A | 7/1987 | Morell |
| 4,688,780 A | 8/1987 | Hanz |
| 4,705,955 A | 11/1987 | Mileikowsky |
| 4,711,578 A | 12/1987 | Chaimowicz |
| 4,752,064 A | 6/1988 | Voss |
| 4,779,858 A | 10/1988 | Saussereau |
| 4,796,613 A | 1/1989 | Heumann et al. |
| 4,819,257 A | 4/1989 | Grasser et al. |
| 4,841,965 A | 6/1989 | Jacobs |
| 4,905,267 A | 2/1990 | Miller et al. |
| 4,917,344 A | 4/1990 | Prechter et al. |
| 4,926,457 A | 5/1990 | Poehner et al. |
| 4,979,519 A | 12/1990 | Chavarria et al. |
| 5,014,290 A | 5/1991 | Moore et al. |
| 5,017,789 A | 5/1991 | Young et al. |
| 5,046,708 A | 9/1991 | Schaefer |
| 5,048,071 A | 9/1991 | Van Steenburg |
| 5,049,147 A | 9/1991 | Danon |
| 5,054,049 A | 10/1991 | Manabe |
| 5,081,665 A | 1/1992 | Kostich |
| 5,090,047 A | 2/1992 | Angotti et al. |
| 5,117,829 A | 6/1992 | Miller et al. |
| 5,156,166 A | 10/1992 | Sebring |
| 5,168,514 A | 12/1992 | Horton, Jr. et al. |
| 5,207,688 A | 5/1993 | Carol |
| 5,230,623 A | 7/1993 | Guthrie et al. |
| 5,240,218 A | 8/1993 | Dye |
| 5,242,455 A | 9/1993 | Skeens et al. |
| 5,269,305 A | 12/1993 | Corol |
| 5,276,927 A | 1/1994 | Day |
| 5,278,886 A | 1/1994 | Ohgushi et al. |
| 5,279,309 A | 1/1994 | Taylor et al. |
| 5,281,232 A | 1/1994 | Hamilton et al. |
| 5,287,576 A | 2/1994 | Fraser |
| 5,297,262 A | 3/1994 | Cox et al. |
| 5,361,765 A | 11/1994 | Herlihy et al. |
| 5,370,117 A | 12/1994 | McLaurin, Jr. |
| 5,370,118 A | 12/1994 | Vij et al. |
| 5,380,336 A | 1/1995 | Misko et al. |
| 5,388,580 A | 2/1995 | Sullivan et al. |
| 5,427,097 A | 6/1995 | Depp |
| 5,446,548 A | 8/1995 | Gerig et al. |
| 5,454,993 A | 10/1995 | Kostich |
| 5,464,411 A | 11/1995 | Schulte et al. |
| 5,485,833 A | 1/1996 | Dietz |
| 5,531,229 A | 7/1996 | Dean et al. |
| 5,538,494 A | 7/1996 | Matsuda |
| 5,549,616 A | 8/1996 | Schulte |
| 5,553,112 A | 9/1996 | Hardy et al. |
| 5,566,681 A | 10/1996 | Manwaring et al. |
| 5,570,409 A | 10/1996 | Yamaguchi et al. |
| 5,588,430 A | 12/1996 | Bova et al. |
| 5,595,191 A | 1/1997 | Kirk |
| 5,622,187 A | 4/1997 | Carol |
| 5,675,851 A | 10/1997 | Feathers |
| 5,676,673 A | 10/1997 | Ferre et al. |
| 5,727,554 A | 3/1998 | Kalend et al. |
| 5,745,545 A | 4/1998 | Hughes |
| 5,751,781 A | 5/1998 | Brown et al. |
| 5,771,512 A | 6/1998 | Kurakake et al. |
| 5,775,337 A | 7/1998 | Hauger et al. |
| 5,797,924 A | 8/1998 | Schulte et al. |
| 5,800,352 A | 9/1998 | Ferre et al. |
| 5,806,116 A | 9/1998 | Oliver et al. |
| 5,820,444 A | 10/1998 | McGaughey |
| 5,820,553 A | 10/1998 | Hughes |
| 5,823,192 A | 10/1998 | Kalend et al. |
| 5,832,550 A | 11/1998 | Hauger et al. |
| 5,848,449 A | 12/1998 | Hauger et al. |
| 5,851,182 A | 12/1998 | Sahadevan |
| 5,865,832 A | 2/1999 | Knopp et al. |
| 5,911,655 A | 6/1999 | Brenneisen |
| 5,947,981 A | 9/1999 | Cosman |
| 5,983,424 A | 11/1999 | Näslund |
| 6,003,174 A | 12/1999 | Kantrowitz et al. |
| 6,023,694 A | 2/2000 | Kouchi et al. |
| 6,026,392 A | 2/2000 | Kouchi et al. |
| 6,085,227 A | 7/2000 | Edlund et al. |
| 6,094,760 A | 8/2000 | Nonaka et al. |
| 6,118,848 A | 9/2000 | Reiffel |
| 6,144,875 A | 11/2000 | Schweikard et al. |
| 6,144,993 A | 11/2000 | Fukunaga et al. |
| 6,148,272 A | 11/2000 | Bergstrom et al. |
| 6,161,237 A | 12/2000 | Tang et al. |
| 6,178,430 B1 | 1/2001 | Cohen et al. |
| 6,181,942 B1 | 1/2001 | Tracy et al. |
| 6,182,060 B1 | 1/2001 | Hedgcock et al. |
| 6,195,578 B1 | 2/2001 | Distler et al. |
| 6,200,025 B1 | 3/2001 | Rich |
| 6,244,745 B1 | 6/2001 | Mattern |
| 6,275,564 B1 | 8/2001 | Ein-Gal |
| 6,279,579 B1 | 8/2001 | Riaziat et al. |
| 6,282,739 B1 | 9/2001 | Livingston |
| 6,308,353 B1 | 10/2001 | Van Steenburg |
| 6,313,915 B1 | 11/2001 | Yanagisawa et al. |
| 6,325,758 B1 | 12/2001 | Carol et al. |
| 6,345,114 B1 | 2/2002 | Mackie et al. |
| 6,375,355 B1 | 4/2002 | Fortin |
| 6,376,846 B2 | 4/2002 | Livingston |
| 6,405,072 B1 | 6/2002 | Cosman |
| 6,446,286 B1 | 9/2002 | Karmalawy |
| 6,452,999 B1 | 9/2002 | Maida |
| 6,460,206 B1 | 10/2002 | Blasche et al. |
| 6,462,553 B1 | 10/2002 | Badura |
| 6,473,490 B1 | 10/2002 | Siochi |
| 6,476,403 B1 | 11/2002 | Dolinskii et al. |
| 6,505,245 B1 | 1/2003 | North et al. |
| 6,509,573 B1 | 1/2003 | Badura et al. |
| 6,565,577 B2 | 5/2003 | Cosman |
| 6,598,275 B1 | 7/2003 | Kolody et al. |
| 6,614,038 B1 | 9/2003 | Brand et al. |
| 6,621,889 B1 | 9/2003 | Mostafavi |
| 6,650,930 B2 | 11/2003 | Ding |
| 6,662,036 B2 | 12/2003 | Cosman |
| 6,670,618 B1 | 12/2003 | Hartmann et al. |
| 6,677,597 B1 | 1/2004 | Haberer et al. |
| 6,690,965 B1 | 2/2004 | Riaziat et al. |
| 6,693,283 B2 | 2/2004 | Eickhoff et al. |
| 6,698,045 B1 | 3/2004 | Coppens et al. |

| Patent | Date | Inventor |
|---|---|---|
| 6,704,957 B2 | 3/2004 | Rhodes |
| 6,725,078 B2 | 4/2004 | Bucholz et al. |
| 6,754,299 B2 | 6/2004 | Patch |
| 6,769,806 B2 | 8/2004 | Moyers |
| 6,780,149 B1 | 8/2004 | Schulte |
| 6,795,523 B2 | 9/2004 | Steinberg |
| 6,799,068 B1 | 9/2004 | Hartmann et al. |
| 6,804,548 B2 | 10/2004 | Takahashi et al. |
| 6,813,788 B2 | 11/2004 | Dinkler et al. |
| 6,814,694 B1 | 11/2004 | Pedroni |
| 6,822,244 B2 | 11/2004 | Beloussov et al. |
| 6,839,404 B2 | 1/2005 | Clark et al. |
| 6,891,177 B1 | 5/2005 | Kraft et al. |
| 6,977,987 B2 | 12/2005 | Yamashita et al. |
| 7,011,447 B2 | 3/2006 | Moyers |
| 7,076,821 B2 | 7/2006 | DeMooy |
| 7,084,410 B2 | 8/2006 | Beloussov et al. |
| 7,120,223 B2 | 10/2006 | Nafstadius |
| 7,142,634 B2 | 11/2006 | Engler et al. |
| 7,154,108 B2 | 12/2006 | Tadokoro et al. |
| 7,154,991 B2 | 12/2006 | Earnst et al. |
| 7,173,265 B2 | 2/2007 | Miller et al. |
| 7,199,382 B2 | 4/2007 | Rigney et al. |
| 7,207,715 B2 | 4/2007 | Yue |
| 7,280,633 B2 | 10/2007 | Cheng et al. |
| 7,301,162 B2 | 11/2007 | Matsuda et al. |
| 7,331,713 B2 * | 2/2008 | Moyers ................... 378/205 |
| 7,348,579 B2 | 3/2008 | Pedroni |
| 7,368,740 B2 | 5/2008 | Beloussov et al. |
| 7,372,053 B2 | 5/2008 | Yamashita et al. |
| 7,398,309 B2 | 7/2008 | Baumann et al. |
| 7,446,328 B2 | 11/2008 | Rigney et al. |
| 7,560,717 B2 | 7/2009 | Matsuda et al. |
| 7,789,560 B2 | 9/2010 | Moyers |
| 2002/0032378 A1 | 3/2002 | Henderson et al. |
| 2002/0051513 A1 | 5/2002 | Pugachev et al. |
| 2002/0065461 A1 | 5/2002 | Cosman |
| 2002/0077545 A1 | 6/2002 | Takahashi et al. |
| 2002/0095730 A1 | 7/2002 | Al-Kassim et al. |
| 2002/0120986 A1 | 9/2002 | Erbel et al. |
| 2002/0188194 A1 | 12/2002 | Cosman |
| 2002/0193685 A1 | 12/2002 | Mate et al. |
| 2003/0007601 A1 | 1/2003 | Jaffray et al. |
| 2003/0031301 A1 | 2/2003 | Longton et al. |
| 2003/0164459 A1 | 9/2003 | Schardt et al. |
| 2004/0013414 A1 | 1/2004 | Karger et al. |
| 2004/0028188 A1 | 2/2004 | Amann et al. |
| 2004/0034438 A1 | 2/2004 | Uematsu |
| 2004/0034932 A1 | 2/2004 | Zacharopoulos et al. |
| 2004/0042583 A1 | 3/2004 | Wackerle et al. |
| 2004/0082856 A1 | 4/2004 | Marmarelis |
| 2004/0098445 A1 | 5/2004 | Baumann et al. |
| 2004/0123388 A1 | 7/2004 | Coppens et al. |
| 2004/0155206 A1 | 8/2004 | Marchand et al. |
| 2004/0158145 A1 | 8/2004 | Ghelmansarai et al. |
| 2004/0164254 A1 | 8/2004 | Beloussov et al. |
| 2004/0174958 A1 | 9/2004 | Moriyama et al. |
| 2004/0184583 A1 | 9/2004 | Nagamine et al. |
| 2005/0054910 A1 | 3/2005 | Tremblay et al. |
| 2005/0072940 A1 | 4/2005 | Beloussov et al. |
| 2005/0116175 A1 | 6/2005 | Haberer |
| 2005/0161618 A1 | 7/2005 | Pedroni |
| 2005/0226377 A1 | 10/2005 | Wong et al. |
| 2005/0281374 A1 | 12/2005 | Cheng et al. |
| 2006/0002511 A1 | 1/2006 | Miller et al. |
| 2006/0017022 A1 | 1/2006 | Rigney et al. |
| 2006/0183960 A1 | 8/2006 | Sioshansi et al. |
| 2007/0018120 A1 | 1/2007 | Beloussov et al. |
| 2007/0018121 A1 | 1/2007 | Leyman et al. |
| 2007/0025524 A1 | 2/2007 | Yue |
| 2007/0031337 A1 | 2/2007 | Schulte |
| 2007/0039621 A1 | 2/2007 | Moyers |
| 2007/0093100 A1 | 4/2007 | Sommer |
| 2007/0108922 A1 | 5/2007 | Amaldi |
| 2007/0158592 A1 | 7/2007 | Hiramoto et al. |
| 2007/0164230 A1 | 7/2007 | Rigney et al. |
| 2007/0262269 A1 | 11/2007 | Trbojevic |
| 2008/0005643 A1 | 1/2008 | Park et al. |
| 2008/0031414 A1 | 2/2008 | Coppens |
| 2008/0042076 A1 | 2/2008 | Miller et al. |
| 2008/0056434 A1 | 3/2008 | Grozinger et al. |
| 2008/0187097 A1 | 8/2008 | Cheng et al. |
| 2008/0189859 A1 | 8/2008 | Sloan et al. |
| 2008/0191142 A1 | 8/2008 | Pedroni |
| 2008/0192892 A1 | 8/2008 | Dilmanian et al. |
| 2008/0237494 A1 | 10/2008 | Beloussov et al. |
| 2008/0292053 A1 | 11/2008 | Marash et al. |
| 2008/0317216 A1 | 12/2008 | Lifshitz et al. |
| 2009/0067577 A1 | 3/2009 | Rigney et al. |
| 2009/0154645 A1 | 6/2009 | Lifshitz et al. |
| 2009/0202045 A1 | 8/2009 | Guertin et al. |
| 2009/0217456 A1 | 9/2009 | Lempen et al. |

FOREIGN PATENT DOCUMENTS

| | | |
|---|---|---|
| DE | 2833800 | 12/1979 |
| DE | 3643893 | 6/1988 |
| DE | 44 18 216 A1 | 11/1995 |
| DE | 19612091 | 3/1997 |
| DE | 102005034912 | 2/2007 |
| EP | 019136 | 11/1980 |
| EP | 247449 | 12/1987 |
| EP | 0 283 082 A1 | 9/1988 |
| EP | 465590 | 1/1992 |
| EP | 480035 | 4/1992 |
| EP | 809525 | 12/1997 |
| EP | 986070 | 3/2000 |
| EP | 986071 | 3/2000 |
| EP | 1064881 | 1/2001 |
| EP | 1454653 | 9/2004 |
| EP | 1584353 | 10/2005 |
| EP | 1585578 | 10/2005 |
| EP | 1709994 | 10/2006 |
| EP | 1792595 | 6/2007 |
| EP | 1795229 | 6/2007 |
| EP | 1900392 | 3/2008 |
| EP | 1935453 | 6/2008 |
| FR | 2701391 | 8/1994 |
| GB | 0870225 | 6/1961 |
| GB | 1362678 | 8/1974 |
| GB | 2213066 | 8/1989 |
| GB | 2254691 | 10/1992 |
| JP | 61194400 | 8/1986 |
| JP | 63-206261 | 8/1988 |
| JP | 3-94736 | 4/1991 |
| JP | 4-339282 | 11/1992 |
| JP | 7-204184 | 8/1995 |
| JP | 2003527763 | 9/2003 |
| NL | 7309246 | 10/1974 |
| WO | WO 8801848 | 3/1988 |
| WO | WO 9011721 | 10/1990 |
| WO | WO 9011723 | 10/1990 |
| WO | WO 9625200 | 8/1996 |
| WO | WO 9852646 | 11/1998 |
| WO | WO 9910137 | 3/1999 |
| WO | WO 0059575 | 10/2000 |
| WO | WO 0100276 | 1/2001 |
| WO | WO 01/89625 A2 | 11/2001 |
| WO | WO 0245793 | 6/2002 |
| WO | WO 03/039212 A1 | 5/2003 |
| WO | WO 03053520 | 7/2003 |
| WO | WO 03076016 | 9/2003 |
| WO | WO 2004026401 | 4/2004 |
| WO | WO 2004032781 | 4/2004 |
| WO | WO 2004060486 | 7/2004 |
| WO | WO 2005018734 | 3/2005 |
| WO | WO 2005018735 | 3/2005 |
| WO | WO 2005037167 | 4/2005 |
| WO | WO 2005102453 | 11/2005 |
| WO | WO 2006060886 | 6/2006 |
| WO | WO 2006076545 | 7/2006 |
| WO | WO 2006094533 | 9/2006 |
| WO | WO 2007012646 | 2/2007 |
| WO | WO 2007016022 | 2/2007 |
| WO | WO 2007054140 | 5/2007 |
| WO | WO 2007061426 | 5/2007 |
| WO | WO 2007062788 | 6/2007 |
| WO | WO 2007068066 | 6/2007 |
| WO | WO2007127970 | 11/2007 |

| WO | WO 2008003526 | 1/2008 |
| WO | WO 2008051358 | 5/2008 |
| WO | WO 2008064271 | 5/2008 |
| WO | WO 2008081480 | 7/2008 |
| WO | WO2008142695 | 11/2008 |

OTHER PUBLICATIONS

"Design of a Proton Therapy Synchrotron" by Fermilab National Accelerator Laboratory, Jun. 1986, LL467-LL574.

"Proceedings of a Medical Workshop on Accelerators for Charged-Particle Beam Therapy" by Fermilab, Jan. 1985, LL33170-LL33313.

"Product Overview" by BrainLAB Radiotherapy Solutions, Copyright 2004 BrainLAB AG.

"Proton Therapy Facility: Engineering Design Report" by Fermi National Accelerator Laboratory, Feb. 1987, LL45441-LL45570.

"Proton Therapy System" by Brobeck Corporation, Nov. 1985, LL54413-LL54459.

Matsu'Ura, Jun, "Systems for Overall Control and Beam Transport of the HIMAC," Mitsubishi Electric Advance, Mitsubishi Electric Corporation, Tokyo, JP, vol. 72, Sep. 1995, pp. 5-7.

European Search Report for Application No. 02789303.1, filed Oct. 28, 2002.

International Search Report for PCT/US02/34556, filed Oct. 28, 2002.

* cited by examiner

FIG. 12

PROVIDING A DEVICE FOR ALIGNING A PATIENT FOR DELIVERING A PLURALITY OF RADIATION BEAMS, THE DEVICE COMPRISING A PATIENT SUPPORT SURFACE, A COARSE ALIGNMENT SUBSYSTEM CONNECTED TO THE PATIENT SUPPORT SURFACE, AND A FINE ALIGNMENT SUBSYSTEM CONNECTED TO THE PATIENT SUPPORT SURFACE

↓

COMPENSATING FOR FLEXION OF THE DEVICE DURING MOVEMENT OF THE DEVICE FROM A FIRST DEVICE POSITION TO A SECOND DEVICE POSITION BY USING A SET OF PREDETERMINED DATA DESCRIBING THE FLEXION BEHAVIOR OF THE DEVICE SO THAT TARGET TISSUE WITHIN THE PATIENT IS PLACED IN THE BEAMLINE CENTER FOR THE DEVICE AT THE SECOND DEVICE POSITION

FIG. 13

PROVIDING A DEVICE FOR ALIGNING A PATIENT FOR DELIVERING A PLURALITY OF RADIATION BEAMS, THE DEVICE COMPRISING PATIENT SUPPORT MEANS, COARSE ALIGNMENT MEANS CONNECTED TO THE PATIENT SUPPORT MEANS, AND FINE ALIGNMENT MEANS CONNECTED TO THE PATIENT SUPPORT MEANS

↓

COMPENSATING FOR FLEXION OF THE DEVICE DURING MOVEMENT OF THE DEVICE FROM A FIRST DEVICE POSITION TO A SECOND DEVICE POSITION BY USING A SET OF PREDETERMINED DATA DESCRIBING THE FLEXION BEHAVIOR OF THE DEVICE SO THAT TARGET TISSUE WITHIN THE PATIENT IS PLACED AT THE BEAMLINE CENTER FOR THE DEVICE AT THE SECOND DEVICE POSITION

FIG.14

COMPENSATING FOR FLEXION OF A RADIATION BEAM DELIVERY DEVICE HAVING A BEAMLINE CENTER DURING MOVEMENT OF THE RADIATION BEAM DELIVERY DEVICE FROM A FIRST DEVICE POSITION TO A SECOND DEVICE POSITION BY USING A SET OF PREDETERMINED DATA DESCRIBING THE FLEXION BEHAVIOR OF THE RADIATION BEAM DELIVERY DEVICE SO THAT THE TARGET TISSUE WITHIN THE PATIENT IS PLACED AT THE BEAMLINE CENTER FOR THE RADIATION BEAM DELIVERY DEVICE AT THE SECOND DEVICE POSITION

FIG. 15 CONTINUED

*CONTINUED FROM SHEET 14/17*

COMPENSATING FOR FLEXION OF THE RADIATION BEAM DELIVERY DEVICE PRODUCED BY THE MOVE TO THE SECOND DEVICE POSITION USING THE DERIVED SET OF PREDETERMINED DATA DESCRIBING THE FLEXION BEHAVIOR OF THE RADIATION BEAM DELIVERY DEVICE TO PLACE THE TARGET TISSUE WITHIN THE PATIENT AT THE BEAMLINE CENTER FOR THE SECOND DEVICE POSITION

DELIVERING A SECOND RADIATION BEAM FROM THE SECOND DEVICE POSITION TO THE TARGET TISSUE WITHIN THE PATIENT

MOVING THE RADIATION BEAM DELIVERY DEVICE TO A THIRD DEVICE POSITION

COMPENSATING FOR FLEXION OF THE RADIATION BEAM DELIVERY DEVICE PRODUCED BY THE MOVE TO THE THIRD DEVICE POSITION USING THE DERIVED SET OF PREDETERMINED DATA DESCRIBING THE FLEXION BEHAVIOR OF THE RADIATION BEAM DELIVERY DEVICE TO PLACE THE TARGET TISSUE WITHIN THE PATIENT AT THE BEAMLINE CENTER FOR THE THIRD DEVICE POSITION

DELIVERING A THIRD RADIATION BEAM FROM THE THIRD DEVICE POSITION TO THE TARGET TISSUE WITHIN THE PATIENT

METHOD AND DEVICE FOR DELIVERING RADIOTHERAPY

CROSS-REFERENCE TO RELATED APPLICATIONS

The present application is a continuation of U.S. patent application Ser. No. 12/033,843, filed Feb. 19, 2008, which is a continuation of U.S. patent application Ser. No. 11/314,138, filed Dec. 21, 2005, now U.S. Pat. No. 7,331,713, which is a continuation of U.S. patent application Ser. No. 10/887,507, filed Jul. 7, 2004, now U.S. Pat. No. 7,011,447, which is a continuation of U.S. application Ser. No. 10/393,836, filed Mar. 20, 2003, now U.S. Pat. No. 6,769,806, which claims priority from International Patent Application PCT/US02/34556, entitled "Method and Device for Delivering Radiotherapy," filed Oct. 28, 2002, which claims the benefit of U.S. Provisional Patent Application 60/340,430, filed Oct. 30, 2001, entitled "Method and Device for Delivering Radiotherapy," the contents of which are incorporated herein by reference in their entirety.

STATEMENT REGARDING FEDERALLY SPONSORED RESEARCH OR DEVELOPMENT

This invention was made with United States Government support under Cooperative Agreement Number DAMD17-97-2-7016 with the National Medical Technology Testbed, Inc., United States Department of the Army. The United States Government has certain rights in this invention.

BACKGROUND OF THE INVENTION

Description of the Related Art

The application of radiation is used for a variety of diagnostic and therapeutic purposes. For example, external radiotherapy known as "teletherapy" is used to treat approximately half of all patients with cancer in the United States, as well as being used to treat patients with arterio-venous malformations, intraocular subfoveal neovascular membranes and Parkinson's disease, among other diseases and conditions.

Generally, teletherapy has been performed using x-ray beams or electron beams. More recently, however, teletherapy has been performed using proton beams due to two characteristics of proton beams. First, proton beams do not scatter as much as either x-ray beams or electron beams. Thus, teletherapy with a proton beam can be applied with a steeper dose gradient near the edge of the proton beam than for an x-ray beam or electron beam. Second, protons lose energy at a more rapid rate as they penetrate tissue, thereby delivering a greater dose at the depth of the target tissue. These two characteristics of proton beams allow the delivery of higher doses to target tissues while minimizing radiation to adjacent normal tissues.

The delineation of target tissues from non-target tissues and the selection of beam directions is typically performed using a computerized treatment planning system. The computerized treatment planning system analyzes input information, such as x-ray axial computed tomography and magnetic resonance imaging, and provides output information, such as beam directions, shapes of normal tissue shields for each beam, and patient alignment information for each beam.

Regardless of the type of teletherapy, however, proper patient alignment is critical to delivering sufficient radiation to target tissues while minimizing radiation delivered to non-target tissues. Patient alignment is the process by which a patient is reproducibly interfaced with the radiation delivery equipment for the purposes of obtaining anatomical, morphological, and physiological information, for performing treatment simulations, and for delivering treatments. The goals of patient alignment are to permit unrestricted access to the patient by radiation beams, and to provide accurate tissue targeting and dose delivery, while promoting patient comfort and safety, and allowing for quick patient egress from the radiation delivery equipment.

The five steps in the patient alignment process are registration, immobilization, localization, positioning and verification. Registration comprises placing the patient on a patient positioner, such as a movable table, in a reproducible manner. Immobilization comprises fixing the registered patient to the patient positioner so that they move together as a single unit in a controlled fashion. Localization comprises determining the location of the target tissue relative to the diagnostic, simulation or treatment unit. Positioning comprises moving the patient positioner to place the target tissue in the desired orientation at the desired location. Verification comprises verifying the patient's orientation and location, and can comprise using the same technique as localization. One or more than one of these steps can be repeated as required. If patient alignment is performed rapidly, the patient is more likely to remain properly aligned, minimizing the margin placed around the target tissue to account for motion and reducing the radiation dose to non-target tissues Patient alignment is usually performed with the patient in a supine position because a larger surface area of the patient is captured by registration and immobilization devices, because the entire patient is at a height more accessible to treatment personnel and because patients are generally more comfortable in the supine position. Most patient positioners have, therefore, been some form of a table.

Registration is typically accomplished using a registration device such as a low-density foam that is custom molded to the patient's shape and attached to the top of the patient positioner. The patient lies directly on the foam, preventing the patient from rolling and translating with respect to the patient positioner, and increasing patient comfort.

Immobilization is typically accomplished using a thermoplastic net that attaches to the patient positioner and that covers both the patient and the registration device. Alternatively, for teletherapy involving the head and neck, immobilization can be accomplished using a ring referred to as a 'halo' that is screwed into the patient's skull and then bolted to the patient positioner.

High precision localization and verification generally rely on radiographic techniques and fiducial markers. The fiducial markers can be internal, such as natural anatomical landmarks or implanted landmarks, or can be external such as a z-box attached to a halo.

Localization and verification for proton beam teletherapy typically uses proton beam treatment units that comprise a diagnostic x-ray source capable of projecting an x-ray beam to simulate the intended path of the proton beam. The x-ray beam passes through the patient creating localization images captured on film or by an electronic portal imaging device. Localization is achieved by comparing the localization images with digitally reconstructed radiographs (DRRS) generated by the treatment planning system. The patient is repositioned iteratively and new localization images are generated until coincidence of the localization images and digitally reconstructed radiographs are obtained thereby verifying the location.

After patient alignment has been completed, teletherapy is commonly performed using isocentric gantries that facilitate the entry of radiation beams into patients from multiple directions in a timely manner. A gantry is a mechanical device that houses a radiation beam delivery system, and comprises one or more than one instrument, such as a particle accelerator, an x-ray tube, a beam spreading device, beam limiting collimators, a particle range modifier, a fluence modifying device and a dose monitoring detector.

The rotation axes of the gantry and the patient positioner intersect at a point in space called the isocenter. The center of the target tissue within the patient is generally placed at the isocenter. Unfortunately, radiation beam delivery devices within the gantry are prone to flex when rotated and, thereby, cause misalignment of the radiation beam with the target tissue.

Historically, when radiation field alignment was not critical to avoid normal tissues adjacent to the target tissues, the edges of radiation fields were placed at large distances around the target tissue volumes to ensure that the target tissue would be hit regardless of the misalignment of the radiation beam due to deflections of the radiation beam delivery system. When critical normal tissues were adjacent to target tissues, however, precise alignment was achieved either by radiographically repositioning the patient for each individual beam or by using large, rigid, and complex mechanical structures to reduce deflections of radiation beam delivery system. Disadvantageously, however, radiographically repositioning a patient requires at least about 15 minutes to align each radiation beam prior to radiation delivery. Therefore, delivering six beams to a patient requires a total treatment time of at least about 1.5 hours. Hence, radiographically repositioning a patient for each radiation beam significantly limits the number of patients that can be treated by each treatment apparatus and increases the cost per treatment.

Therefore, it would be useful to have a method of aligning a patient for delivering multiple radiation beams, such as proton beams, that allows a patient to be aligned in less time between beam deliveries. Further, It would be useful to have a device for aligning a patient for delivering multiple radiation beams, such as proton beams, that allows a patient to be aligned in less time.

SUMMARY OF THE INVENTION

According to one embodiment of the present invention, there is provided a device for aligning a patient for delivering a plurality of radiation beams. The device comprises a patient support surface, a coarse alignment subsystem connected to the patient support surface, and a fine alignment subsystem connected to the patient support surface. In one embodiment, the patient support surface comprises a table. In another embodiment, the coarse alignment subsystem can induce coarse movements of the patient support surface comprising translation motions of as large as about 2 m, and rotations of as large as about 60°. In another embodiment, the coarse alignment subsystem comprises an elevating column. In another embodiment, the coarse alignment subsystem further comprises a base and a plurality of wheels connected to the base. In another embodiment, the coarse alignment subsystem further comprises a base and a counterweight connected to the base. In another embodiment, the device further comprises electronics to control movement of the coarse alignment subsystem. In another embodiment, the coarse alignment subsystem comprises a position detection system to calculate the position of the device. In another embodiment, the device further comprises an interface for affixing one or more than one registration and immobilization device connected to the patient support surface. In a preferred embodiment, the fine alignment subsystem can induce fine movements of the patient support surface comprising translation motions as large as about ±20 mm with a resolution of between about 0.04 mm and 0.1 mm resolution in three perpendicular axes, and pitch and roll rotations as large as about ±5° with a resolution of between about 0.1° and 0.2°. In another preferred embodiment, the fine alignment subsystem can induce fine movements of the patient support surface comprising translation motions as large as about ±20 mm with about 0.05 mm resolution in three perpendicular axes, and pitch and roll rotations of as large as about ±5° with a resolution of about 0.1°. In another embodiment, the device further comprises electronics to control movement of the fine alignment subsystem.

According to another embodiment of the present invention, there is provided a device for aligning a patient for delivering a plurality of radiation beams comprising patient support means, coarse alignment means connected to the patient support means, and fine alignment means connected to the patient support means. In one embodiment, the patient support means comprises a table. In another embodiment, the coarse alignment subsystem can induce coarse movements of the patient support surface comprising translation motions of as large as about 2 m, and rotations of as large as about 60°. In another embodiment, the coarse alignment means comprises an elevating column. In another embodiment, the coarse alignment means further comprises a base and a plurality of wheels connected to the base. In another embodiment, the coarse alignment means further comprises a base and a counterweight connected to the base. In another embodiment, the device further comprises electronics to control movement of the coarse alignment means. In another embodiment, the coarse alignment means comprises a position detection system to calculate the position of the device. In another embodiment, the device further comprises an interface for affixing one or more than one registration and immobilization means connected to the patient support means. In a preferred embodiment, the fine alignment subsystem can induce fine movements of the patient support surface comprising translation motions as large as about ±20 mm with a resolution of between about 0.04 mm and 0.1 mm resolution in three perpendicular axes, and pitch and roll rotations as large as about ±5° with a resolution of between about 0.1° and 0.2°.

According to another embodiment of the present invention, there is provided a method of aligning a patient for delivering a plurality of radiation beams from a plurality of device positions comprising providing a device of the present invention. In one embodiment, the device has a beamline center, and the method additionally comprises compensating for flexion of the device during movement of the device from a first device position to a second device position by using a set of predetermined data describing the flexion behavior of the device so that target tissue within the patient is placed at the beamline center for the device at the second device position.

According to another embodiment of the present invention, there is provided a method of aligning a patient for delivering a plurality of radiation beams from a plurality of device positions comprising compensating for flexion of a radiation beam delivery device having a beamline center during movement of the radiation beam delivery device from a first device position to a second device position by using a set of predetermined data describing the flexion behavior of the radiation beam delivery device so that the target tissue within the patient is placed at the beamline center for the radiation beam delivery device at the second device position.

According to another embodiment of the present invention, there is provided a method of aligning a patient with a target tissue within the patient for delivering a plurality of radiation beams from a plurality of device positions. The method comprises, a) providing a radiation beam delivery device having a beamline center; b) deriving a set of predetermined data describing the flexion behavior of a radiation beam delivery device; c) selecting a patient having one or more than one target tissue suitable for receiving a plurality of radiation beams; d) producing a treatment plan; e) aligning the patient with respect to the radiation beam delivery device oriented at a first device position using the derived set of predetermined data describing the flexion behavior of the radiation beam delivery device to place the target tissue within the patient at the beamline center for the first device position; f) delivering a first radiation beam from the first device position to the target tissue; g) moving the radiation beam delivery device to a second device position; h) compensating for flexion of the radiation beam delivery device produced by the move to the second device position using the derived set of predetermined data describing the flexion behavior of the radiation beam delivery device to place the target tissue within the patient at the beamline center for the second device position; and i) delivering a second radiation beam from the second device position to the target tissue within the patient. In one embodiment, the method further comprises a) moving the radiation beam delivery device to a third device position; b) compensating for flexion of the radiation beam delivery device produced by the move to the third device position using the derived set of predetermined data describing the flexion behavior of a radiation beam delivery device to place the target tissue within the patient at the beamline center for the third device position; and c) delivering a third radiation beam from the third device position to the target tissue within the patient. In another embodiment, selecting a patient having one or more than one target tissue suitable for receiving a plurality of radiation beams comprises selecting a patient having one or more than one target tissue having a disease or condition amenable to teletherapy. The disease or condition can be selected from the group consisting of acoustic neuroma, adenocarcinoma, astrocytoma, chordoma, meningioma, nasopharyngeal carcinoma and pituitary adenoma. In another embodiment, aligning the patient with respect to the radiation beam delivery device oriented at a first device position comprises using a two-stage patient positioner. In another embodiment, compensating for flexion of the radiation beam delivery device produced by the move to the second device position comprises using a two-stage patient positioner and moving the patient and patient positioner as a unit. In another embodiment, compensating for flexion of the radiation beam delivery device produced by the move to the second device position comprises one or more than one action selected from the group consisting of shifting an aperture or block holding cone with respect to the beam delivery apparatus center, shifting the position of beam delivery apparatus defining collimators, and offsetting the scan pattern of a magnetically scanned beam.

BRIEF DESCRIPTION OF THE DRAWINGS

These and other features, aspects and advantages of the present invention will become better understood with regard to the following description, appended claims, and accompanying figures where:

FIG. 12, FIG. 13, FIG. 14 and FIG. 15 are flow charts depicting some steps of various embodiments of the method of the present invention.

DETAILED DESCRIPTION OF THE PREFERRED EMBODIMENT

According to one embodiment of the present invention, there is provided a device for aligning a patient for delivering a plurality of radiation beams, such as proton beams, from a radiation beam delivery device at a plurality of device positions that allows a patient to be aligned in less time than using conventional aligning devices. According to another embodiment of the present invention, there is provided a method of aligning a patient for delivering a plurality of radiation beams, such as proton beams, from a radiation beam delivery device at a plurality of device positions. The method allows a patient to be aligned in less time than using conventional methods. By reducing the amount of time for alignment, both the device and the method allow an increased number of patients to be treated, decrease the cost of treatment per patient, and reduce the amount of radiation exposure to non-target tissues resulting from the alignment process. According to another embodiment of the present invention, there is provided a method of performing teletherapy. The method of performing teletherapy comprises aligning a patient using the method of aligning of the present invention and delivering a plurality of radiation beams from two or more than two directions. Though disclosed in connection with teletherapy, and especially teletherapy utilizing proton beams, the device and method can also be used for aligning a patient for delivering other kinds of radiation accurately and rapidly to a circumscribed area, for purposes other than teletherapy, as will be understood by those with skill in the art with reference to this disclosure.

In one embodiment, the present invention is a device for aligning a patient for delivering a plurality of radiation beams that takes less time to align the patient between each beam delivery than using conventional devices. The device can be used with the method of the present invention.

The device comprises a two-stage patient positioner. One stage comprises a coarse alignment subsystem capable of providing large traversals (defined as greater than about 2 m) and large rotations (defined as greater than about 5°) within the treatment room to place target tissue within the patient near the isocenter. The second stage comprises a fine alignment subsystem capable of submillimeter translations and subdegree size rotations to correct for any initial misalignments near isocenter, and to compensate for any deflections in the beam delivery device when a plurality of radiation beams is applied to the target tissue from a plurality of delivery directions.

Figure 1:
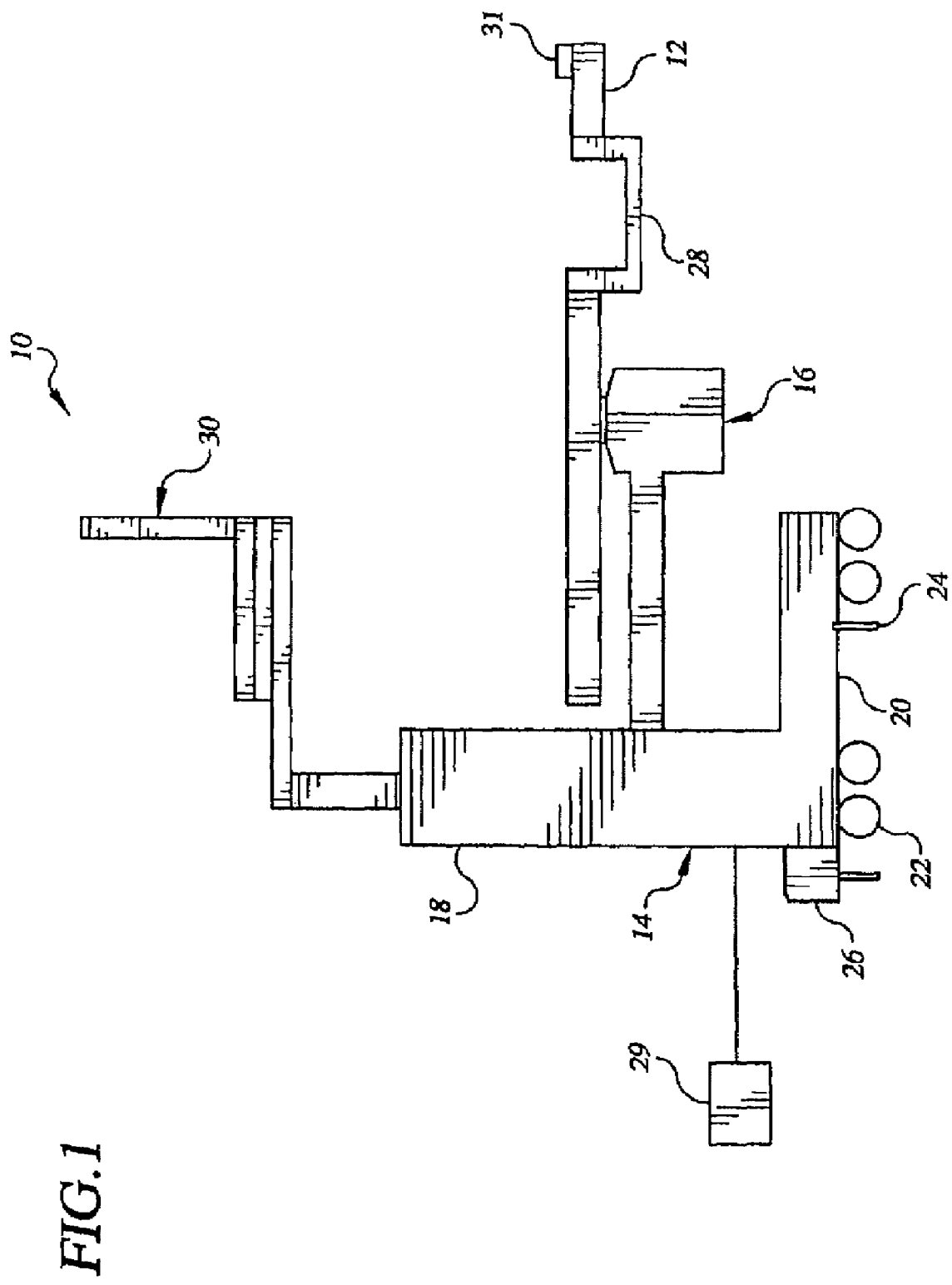
FIG. 1 is a schematic view of one embodiment of the device for aligning a patient for delivering multiple radiation beams according to the present disclosure.

Referring now to FIG. 1, there is shown a schematic view of one embodiment of the device of the present invention. As can be seen, the device 10 comprises a patient support surface 12, a coarse alignment subsystem 14 connected to the patient support system 12 and a fine alignment subsystem 16 connected to the patient support surface 12.

The coarse alignment subsystem 14 induces coarse movements of the patient support surface 12 around the treatment room. In a preferred embodiment, the coarse alignment subsystem 14 can induce coarse movements of the patient support surface 12 that comprise traversals as large as about 4 m and rotations as large as about 200°. In another preferred embodiment, the coarse alignment subsystem 14 can induce coarse movements of the patient support surface 12 that comprise traversals as large as about 2 m and rotations as large as about 60°. In a particularly preferred embodiment, the coarse alignment subsystem 14 can induce coarse movements of the patient support surface 12 that comprise traversals as large as about 1 m and rotations as large as about 10°.

As shown in FIG. 1, the coarse alignment subsystem 14 comprises an elevating column 18 connected to the fine alignment subsystem 16, and connected to a base 20. The coarse alignment subsystem 14 preferably further comprises a plurality of wheels 22 attached to the base 20, which permit the device 10 to translocate around the treatment room. In one embodiment, the wheels 22 are computer controlled. In another embodiment, the coarse alignment subsystem 14 comprises base stand locks 24 to maintain a selected position of the device 10 in the treatment room. In a preferred embodiment, the coarse alignment subsystem 14 comprises a counterweight 26 connected to the base 20 to counterbalance the weight of the patient support surface 12 and a patient (not shown). Preferably, the coarse alignment subsystem 14 additionally comprises electronics 29 to control movement of the coarse alignment subsystem 14. In one embodiment, the coarse alignment subsystem 14 further comprises a position detection system 30 to calculate the position of the device 10 in the treatment room. A suitable coarse alignment subsystem 14, including a position detection system 30, can be obtained from ONCOlog Medical QA AB of Uppsala, Sweden under the name Hercules, though the belt and belt power stage do not need to be installed for incorporation into the device 10, and the beam axis feature does not need to be used for the device 10. Other commercially available coarse alignment subsystems and position detection systems are also suitable, as will be understood by those with skill in the art with reference to this disclosure.

Figure 1A:
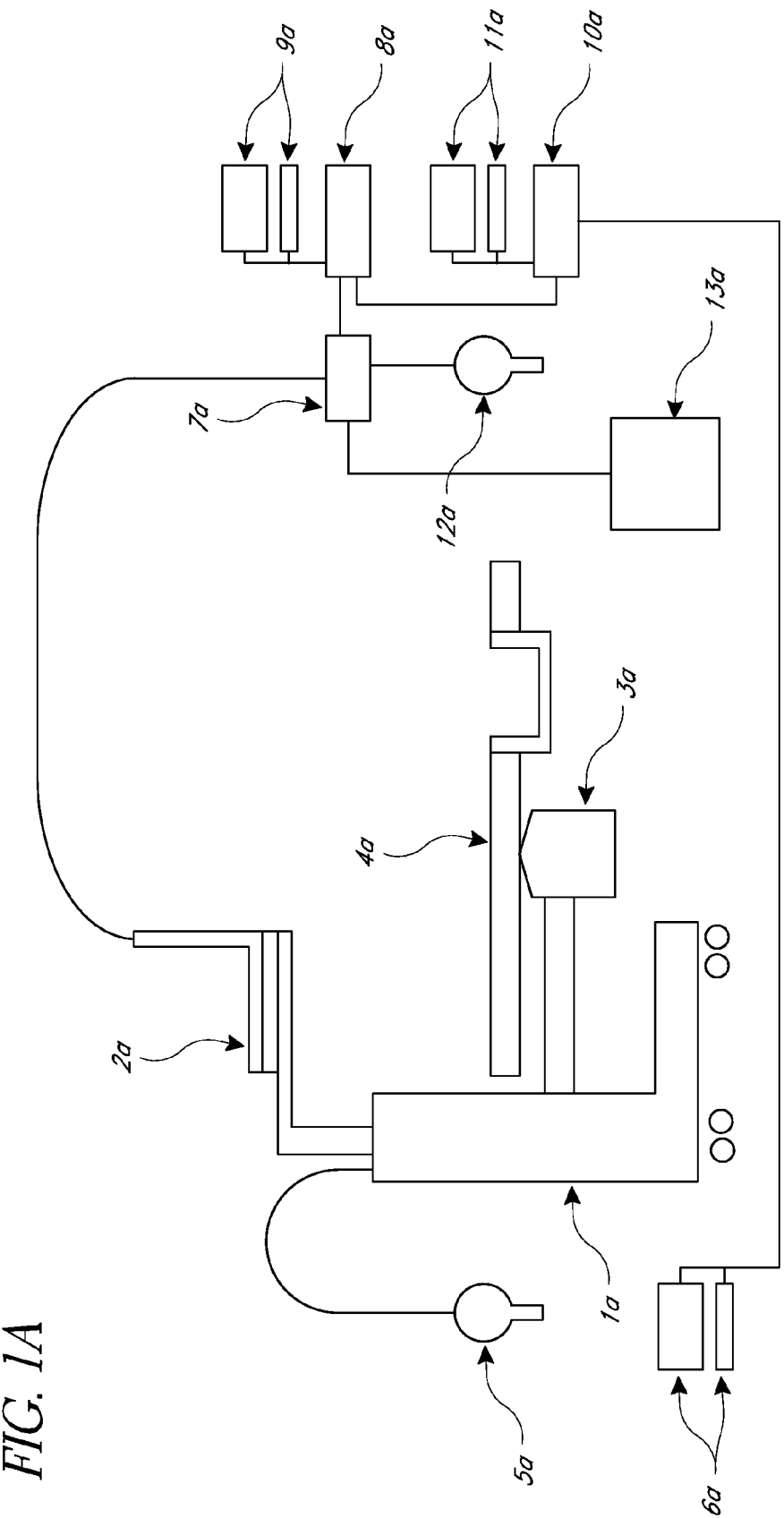
FIG. 1A is a schematic view of an embodiment of a device for aligning a patient for delivering multiple beams of radiation.

FIG. 1A illustrates a device for aligning a patient for delivering multiple beams of radiation that takes less time to align the patient than using conventional methods. The device can be used with the methods of the present disclosure.

With further reference to FIG. 1A, the device comprises a two-stage patient positioner. One stage comprises a coarse alignment subsystem capable of providing large traversals (greater than about 2 m) and rotations within the treatment room to place the target within the patient near the nominal exposure location. The other stage comprises a fine alignment sub-system capable of submillimeter translations and subdegree rotations to correct for initial miss-alignments near the nominal exposure location, provide proper orientation, and to compensate for deflections in the beam delivery apparatus when multiple field directions are applied.

With reference to FIG. 1A, there is shown a schematic view of one embodiment of the device. As can be seen, the device is a two-stage patient positioner that comprises a traveling base stand 1a, a base stand and position detection system 2a, a fine alignment sub-system 3a, a table top 4a, a treatment room patient positioner manual controls, a treatment room user interface monitor and keyboard 6a, a patient positioner control system interface 7a, a real time patient positioner control system computer 8a, a real time patient positioner control system monitor and keyboard 9a, a user interface and patient database computer 10a, a control room user interface monitor and keyboard 11a, a control room patient positioner manual control 12a and a treatment beam control system 13a.

With further reference to FIG. 1A, the traveling base stand 1a provides coarse movements around the treatment room. It comprises an elevating column, three pairs of computer controlled wheels, electronics, and counterweight for the cantilevered table top and patient. Vertical stability of the patient positioner during motion is dependent on the floor under the patient positioner being level to within 0.2 mm. This is achieved using an epoxy mix prior to installation of the patient positioner according to techniques known to those with skill in the art.

With further reference to FIG. 1A, the base stand position detection system 2a comprises several fixed length articulating arms and rotational encoders that are used to calculate the position of the patient positioner in the treatment room. A suitable base stand and position detection system can be obtained from Precitron AB of Uppsala, Sweden under the brand name Hercules®, though other units are also suitable as will be understood by those with skill in the art with reference to this disclosure.

With further reference to FIG. 1A, the fine alignment subsystem 3a provides pitch and roll rotations up to about ±5 0 with a resolution of about 0.10 and three perpendicular translation motions of about ±20 mm with about 0.05 mm resolution. The speed of patient positioner motions is preferably as fast as possible, without displacing patients from their registration device, therefore, the speed is preferably controlled manually by the treatment personnel using an adjustable hand control.

With further reference to FIG. 1A, the table top 4a is a patient support, such as a Atlas® table top from Precitron AB, that has affixed to it various registration and immobilization devices such as whole body pods, foam cradles, face masks, cranial halos, and bite blocks. Interfaces for these devices allow their rapid exchange. The table top 4a further comprises an opposing pair of C-shaped bars that link one part of the table to another along its longitudinal length. As shown, the bars provide an open area that allows radiation beams to pass, while the patient is supported by the registration devices. In a preferred embodiment, the C-shaped arms can be rotated away from the beam path while the patient is registered and immobilized on the table top 4a. With the arms rotated outward and positioned laterally, the open area in which a beam can pass is preferably about 500 mm by 500 mm. With the arms rotated inward, oblique beams with large field sizes may be used.

With further reference to FIG. 1A, the treatment room patient positioner manual control 5 allows direct movement of base sub-system motions and provides enable switches for execution of automatic set-up features, the fine alignment subsystem motions and the compensation moves.

With further reference to FIG. 1A, the patient positioner control system interface 7a distributes power and safety signals and links the real time patient positioner control system computer 8a to the position sensors and drive motors of the base stand 1a, base stand position detection system 2a, and fine alignment sub-system 3a. Both the control system interface 7a and real time computer 8a have been expanded from the standard Hercules configuration to accept the additional signals and commands coming from and going to the fine alignment system. The real time patient positioner control system and keyboard 9a are used for set-up and calibration of the patient positioner.

With further reference to FIG. 1A, the user interface and patient database computer 10a stores the beam delivery system deflection database, runs the compensation algorithm, and stores and downloads patient position files. The treatment room user interface monitor and keyboard 6a and control room user interface monitor and keyboard 11a allow entering patient data and selected patient positioner motions, and are identical except for their location in the treatment room and control room, respectively. The initial alignment is performed using the x-ray image data in using the treatment room user interface monitor and keyboard 6a. Multiple subsequent fields are then treated without entering the treatment room using the control room user interface monitor and keyboard 11a. Safety of the patient, treatment personnel and equipment is enhanced by requiring activation of enable switches on the treatment room patient positioner manual control 5a or on the control room patient positioner manual control 12a.

Figure 2:
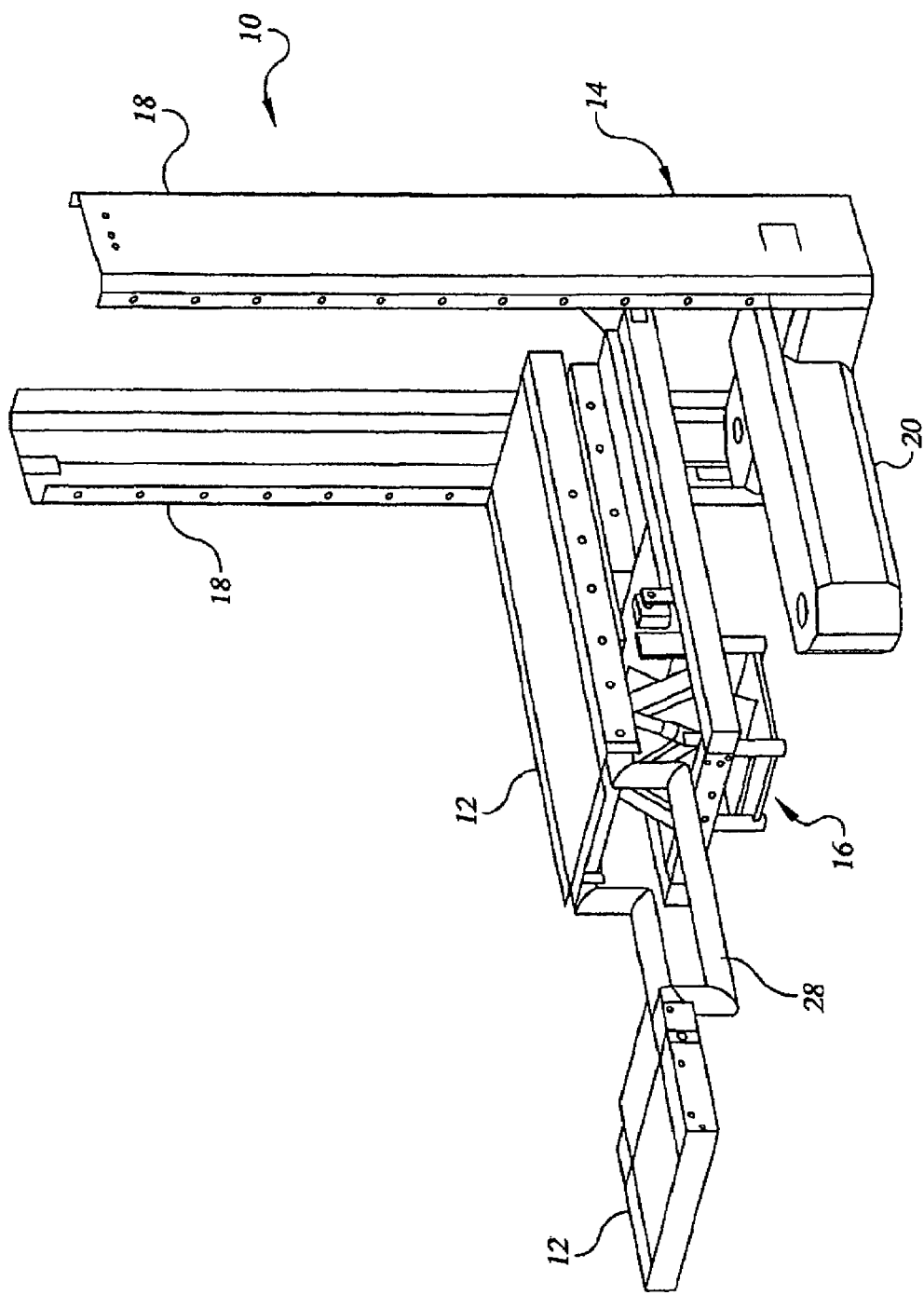
FIG. 2 is a perspective lateral view of the device in FIG. 1 with the patient support surface in a neutral position.

Referring now to FIG. 2, there is shown a perspective side elevational view of the device 10. As can be seen, the device 10 further comprises a patient support surface 12, such as a table. As shown in FIG. 2, the patient support surface 12 is in a neutral position, that is, parallel to the long axis of the base 20 and perpendicular to the long axis of the elevating column 18. A suitable table is the Atlas patient support surface from ONCOlog Medical QA AB, though other patient support surfaces are also suitable, as will be understood by those with skill in the art with reference to this disclosure.

In a preferred embodiment, the device 10 has interfaces 31 for affixing one or more than one registration and immobilization devices, such as whole body pods, foam cradles, face masks, cranial halos and bite blocks. In another preferred embodiment, as shown, the patient support surface 12 comprises an opposing pair of C-shaped arms 28 that link one part of the patient support surface 12 to another part along its longitudinal length and that allow the distal end of the patient support surface 12 to extend distally, creating an open area that allows a radiation beam to pass into the target tissue unimpeded while the patient remains supported by one or more than one registration device. Preferably, the C-shaped arms 28 can be rotated away from the beam path while the patient is registered and immobilized on the patient support surface 12.

The device 10 further comprises a fine alignment subsystem 16 connected to the patient support surface 12 and to the coarse alignment subsystem 14. The fine alignment subsystem 16 induces fine movements of the patient support surface 12 with respect to the treatment room. In one embodiment, the fine movements comprise translation motions of as large as about ±20 mm with between about 0.04 mm and 0.1 mm resolution in three perpendicular axes, and pitch and roll rotations of as large as about ±5° with a resolution of between about 0.1° and 0.2°. In a preferred embodiment, the fine movements comprise translation motions of as large as about ±20 mm with about 0.05 mm resolution in three perpendicular axes, and pitch and roll rotations of as large as about ±5° with a resolution of about 0.1°.

Figure 3:
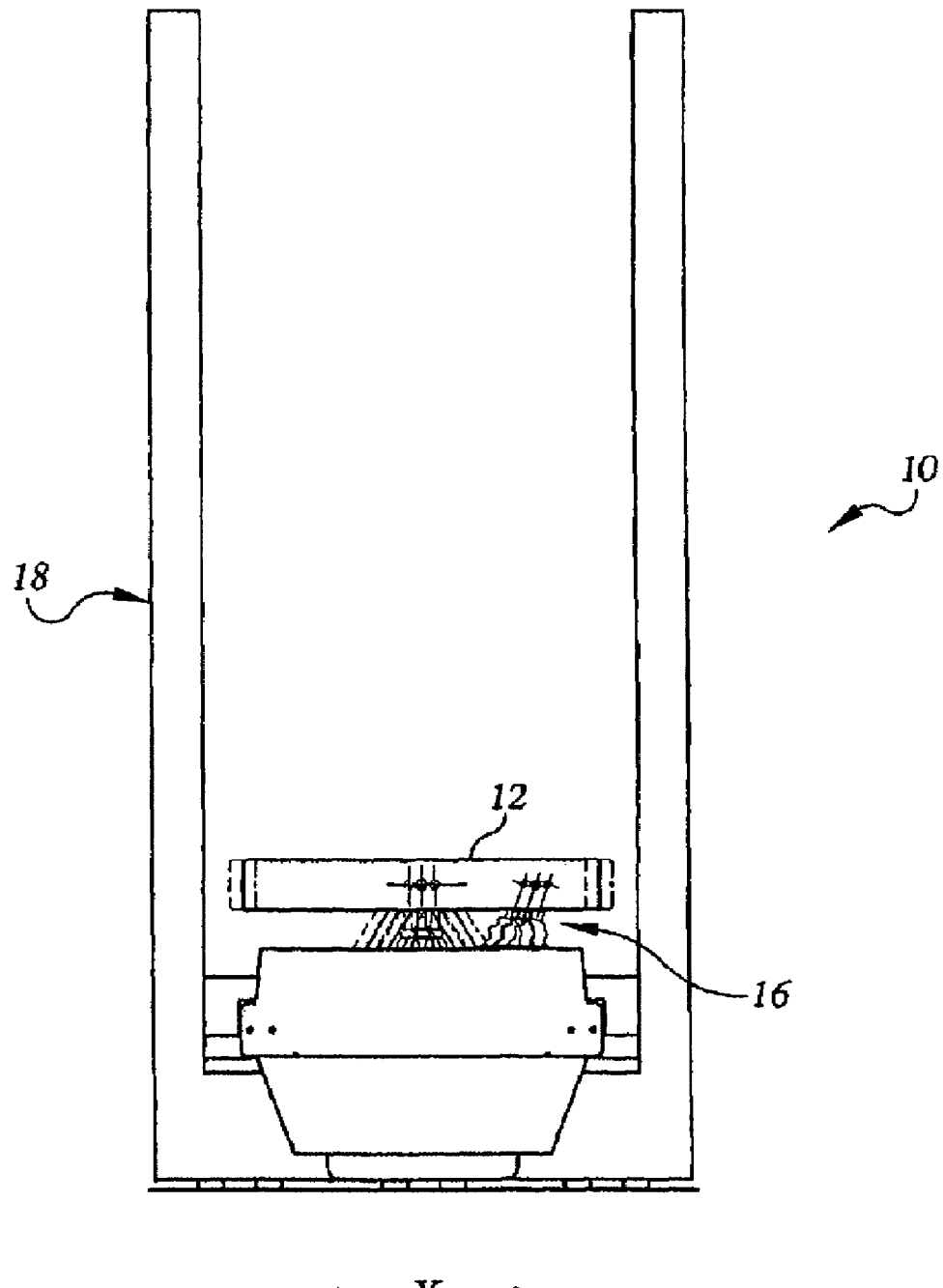
FIG. 3 is a side elevational schematic view of the device in FIG. 1 showing fine movement of the device in the x-axis.
Figure 4:
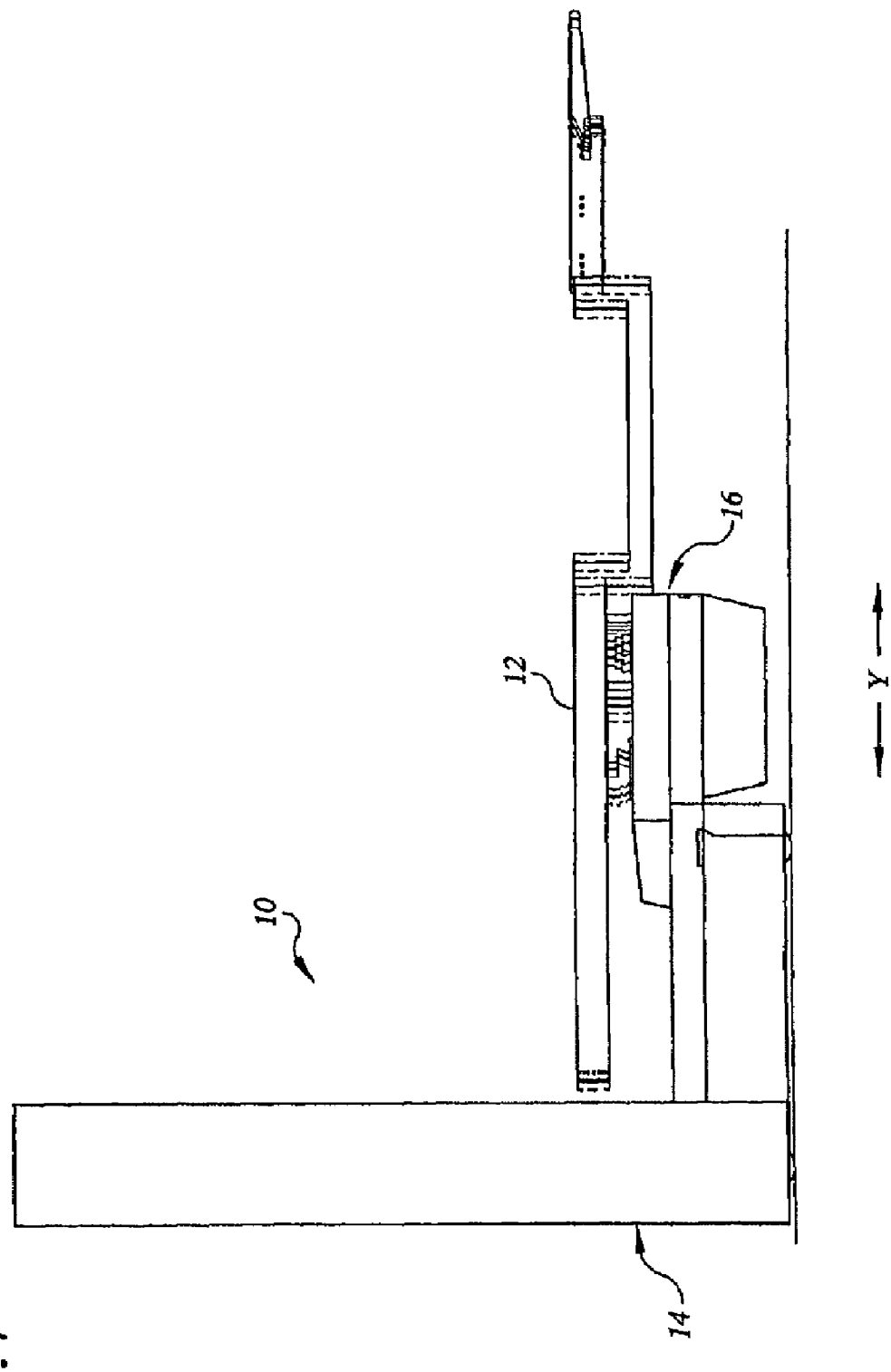
FIG. 4 is a side elevational schematic view of the device in FIG. 1 showing fine movement of the device in the y-axis.
Figure 5:
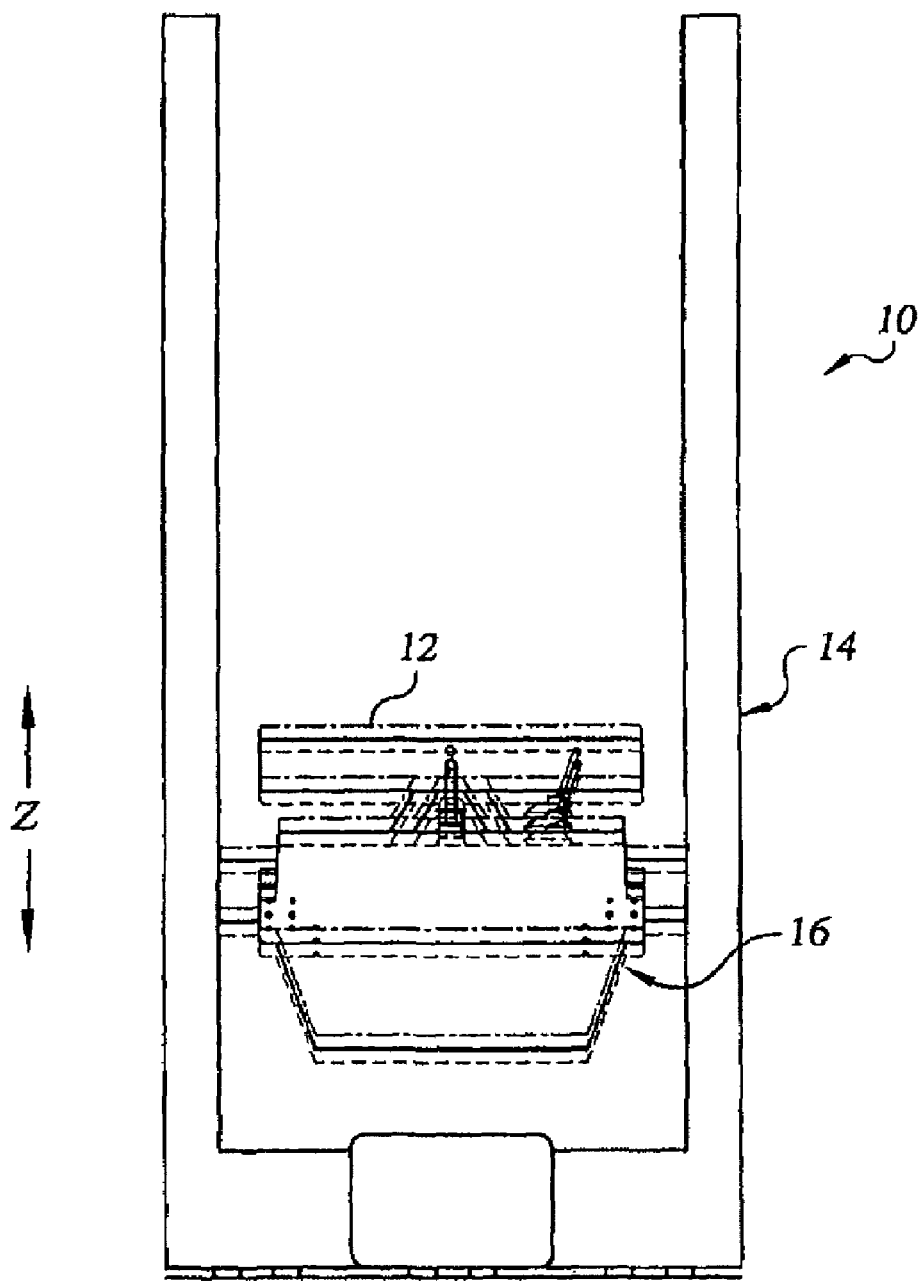
FIG. 5 is a side elevational schematic view of the device in FIG. 1 showing fine movement of the device in the z-axis.
Figure 6:
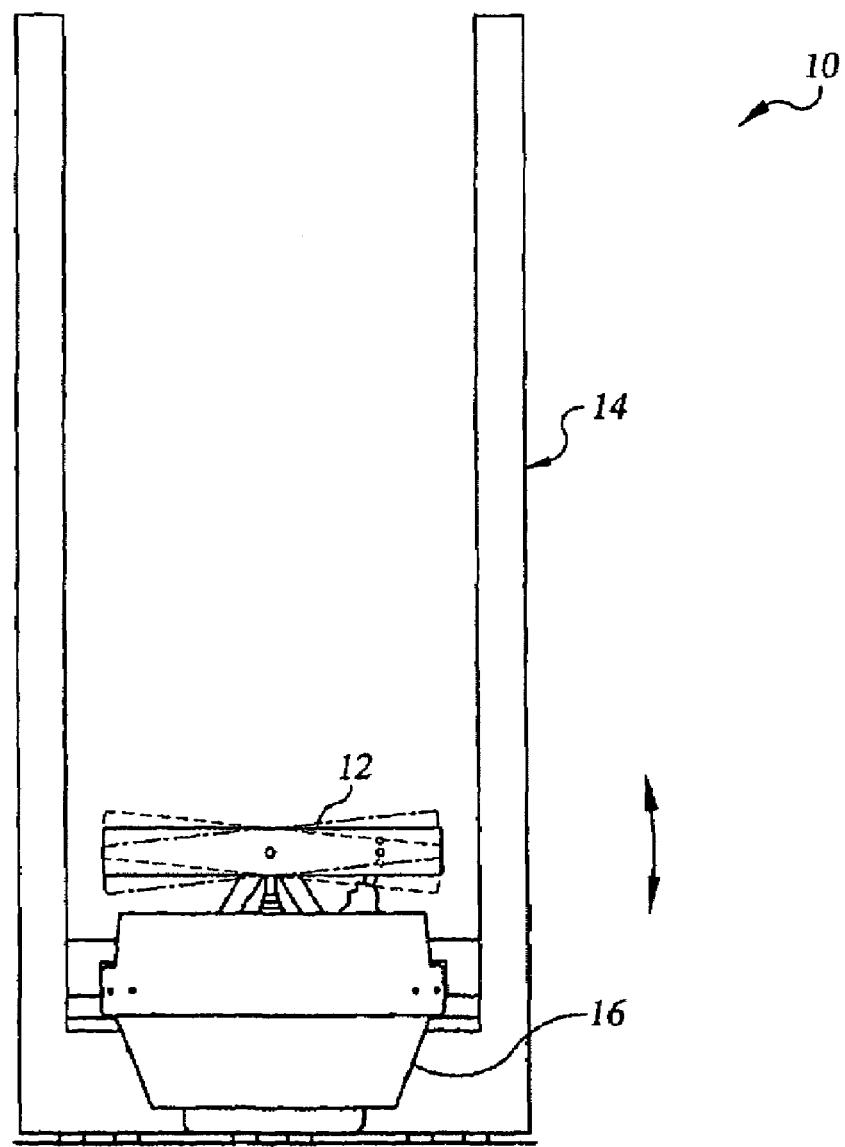
FIG. 6 is a side elevational schematic view of the device in FIG. 1 showing fine movement of the device in a roll motion.
Figure 7:
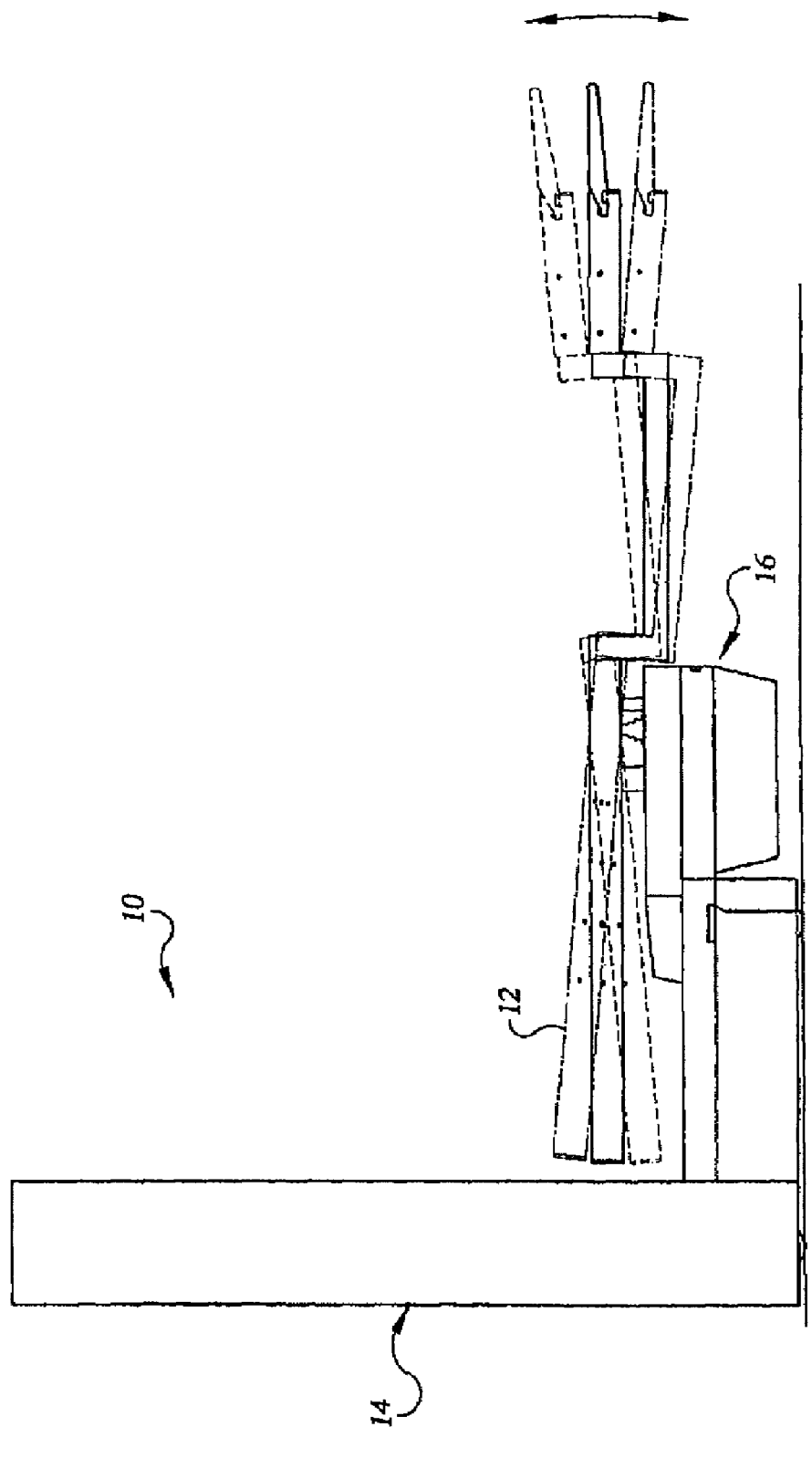
FIG. 7 is a side elevational schematic view of the device in FIG. 1 showing fine movement of the device in a pitch motion.

Referring now to FIG. 3 through FIG. 7, there are shown side elevational schematic views of the device 10 showing: fine movement of the device 10 in the x-axis, FIG. 3; fine movement of the device 10 in the y-axis, FIG. 4; fine movement of the device 10 in the z-axis, FIG. 5; fine movement of the device 10 in a roll motion, FIG. 6; and fine movement of the device 10 in a pitch motion, FIG. 6.

Figure 8:
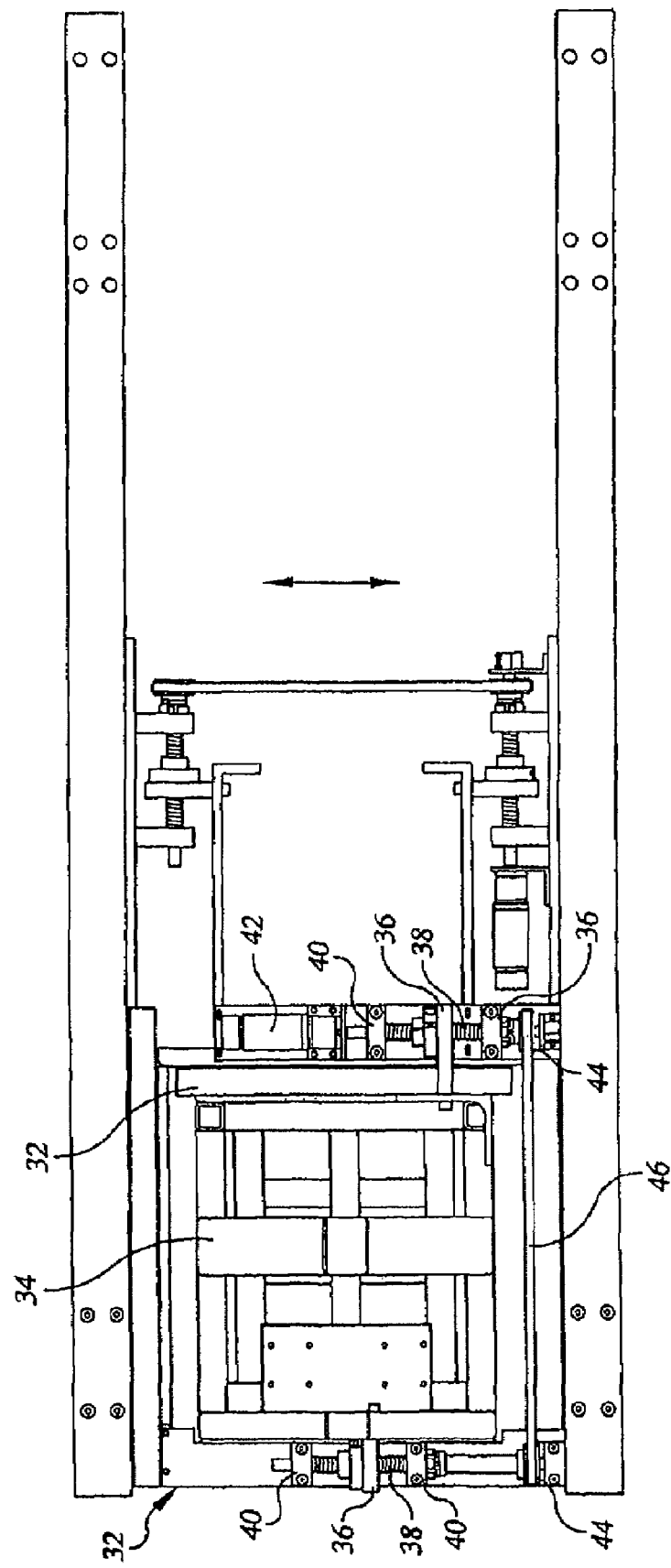
FIG. 8 is a top cutaway, schematic view of the device in FIG. 1 illustrating an example of the components of the device in FIG. 1 allowing for fine movement in the x-axis.

Referring now to FIG. 8, there is shown a top cutaway, schematic view of the device 10 illustrating an example of the components of the device 10 allowing for fine movement in the x-axis. As can be seen, the components of the device 10 allowing for fine movement in the x-axis comprise rails 32, an x-carrier 34, a driver slot with a ball nut 36, a ball screw 38, a bearing holder 40, a motor with gearbox 42, belt pulleys 44, a synchronizing belt 46, and a 10-turn precision potentiometer 48.

Figure 9:
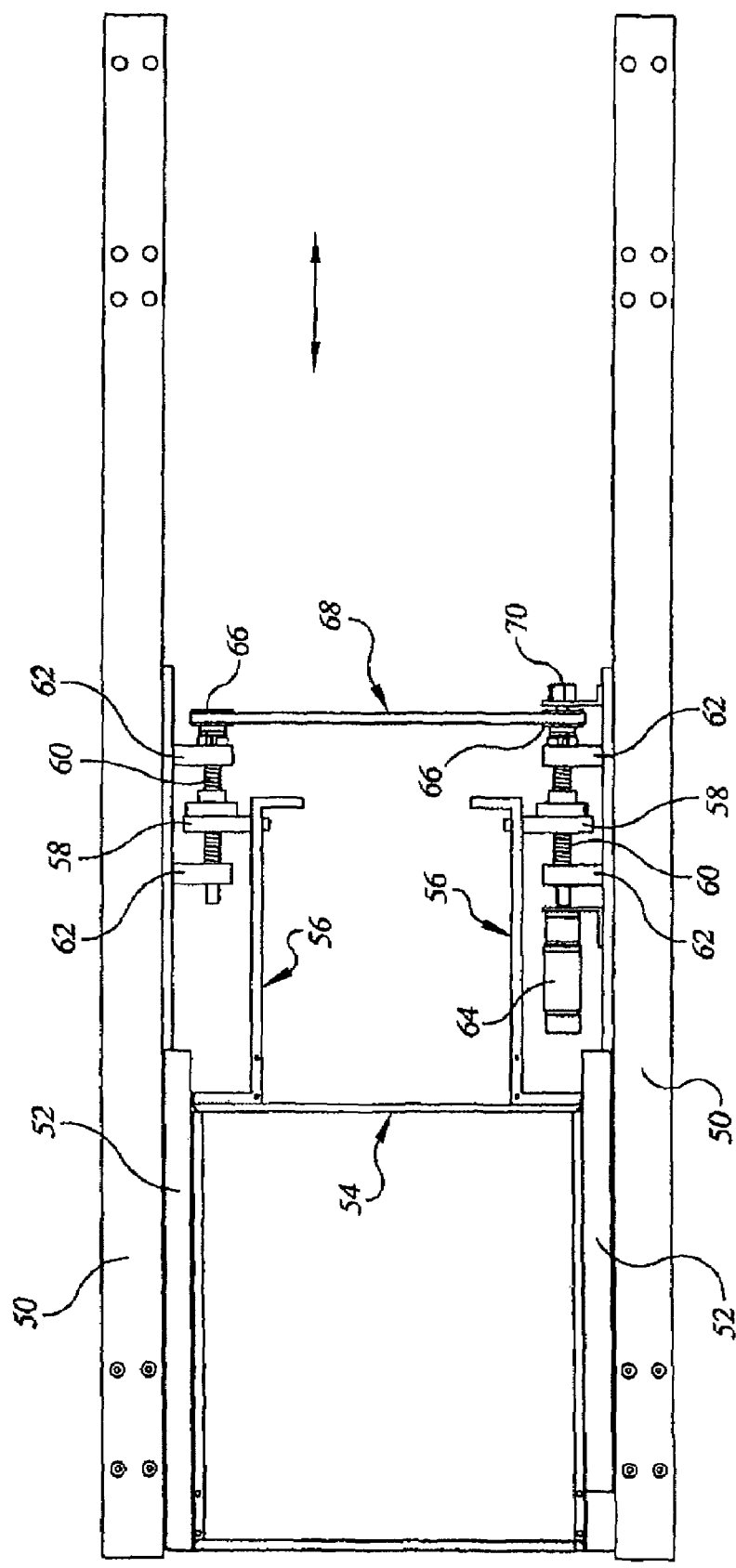
FIG. 9 is a top cutaway, schematic view of the device in FIG. 1 illustrating an example of the components of the device in FIG. 1 allowing for fine movement in the y-axis.

Referring now to FIG. 9, there is shown a top cutaway, schematic view of the device 10 illustrating an example of the components of the device 10 allowing for fine movement in the y-axis. As can be seen, the components of the device 10 allowing for fine movement in the y-axis comprise a framework 50, rails 52, a y-carrier 54, a support driver 56, a driver slot with a ball nut 58, a ball screw 60, a bearing holder 62, a motor with gearbox 64, belt pulleys 66, a synchronizing belt 68, and a 10-turn precision potentiometer 70.

Figure 10:
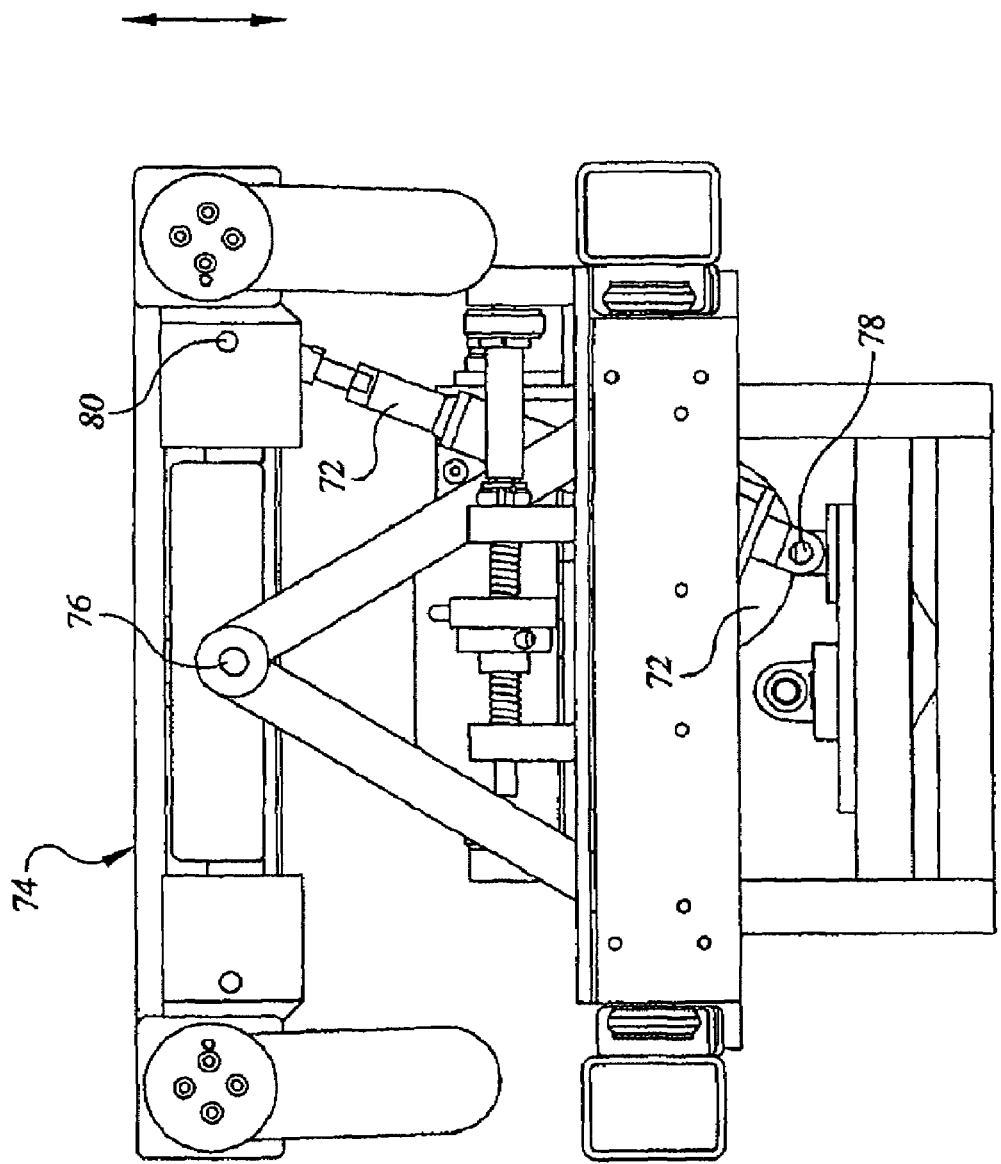
FIG. 10 is a top cutaway, schematic view of the device in FIG. 1 illustrating an example of the components of the device in FIG. 1 allowing for fine roll movement.

Referring now to FIG. 10 there is shown a lateral cutaway, schematic view of the device 10 illustrating an example of the components of the device 10 allowing for fine roll movement. As can be seen, the components of the device 10 allowing for fine roll movement comprise a linear actuator 72, a tabletop 74, a center of rotation for roll angle 76, a lower center of rotation for the actuator 78, and an upper center of rotation for the actuator 80. Also shown are the C-shaped arms 28.

Figure 11:
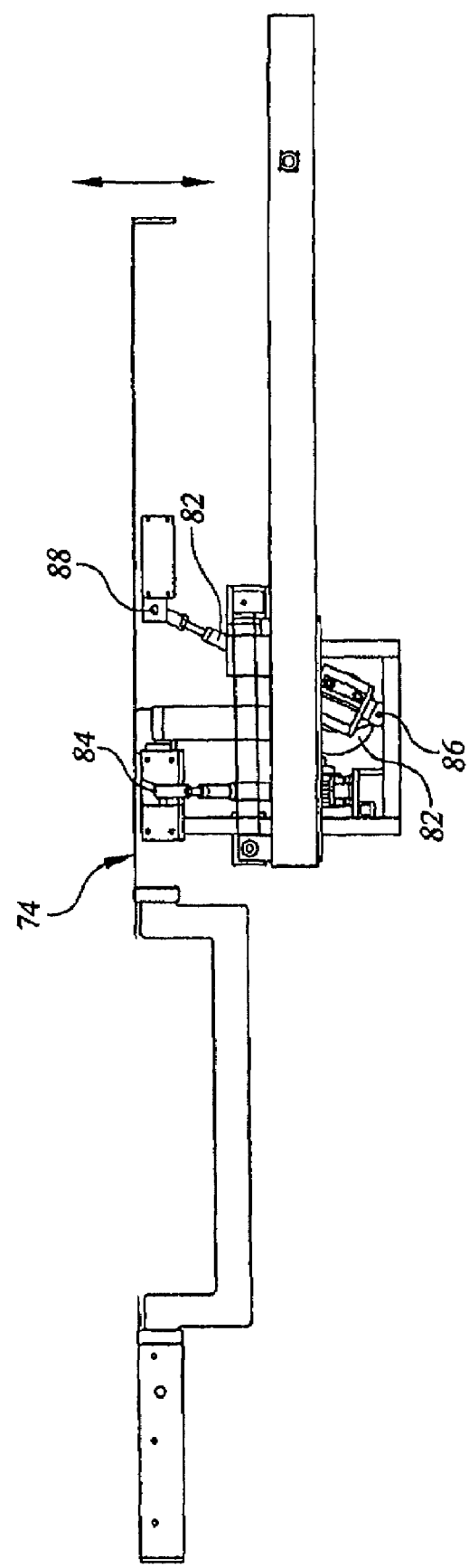
FIG. 11 is a perspective cutaway, schematic view of the device in FIG. 1 illustrating an example of the components of the device in FIG. 1 allowing for fine pitch movement.
Figure 15:
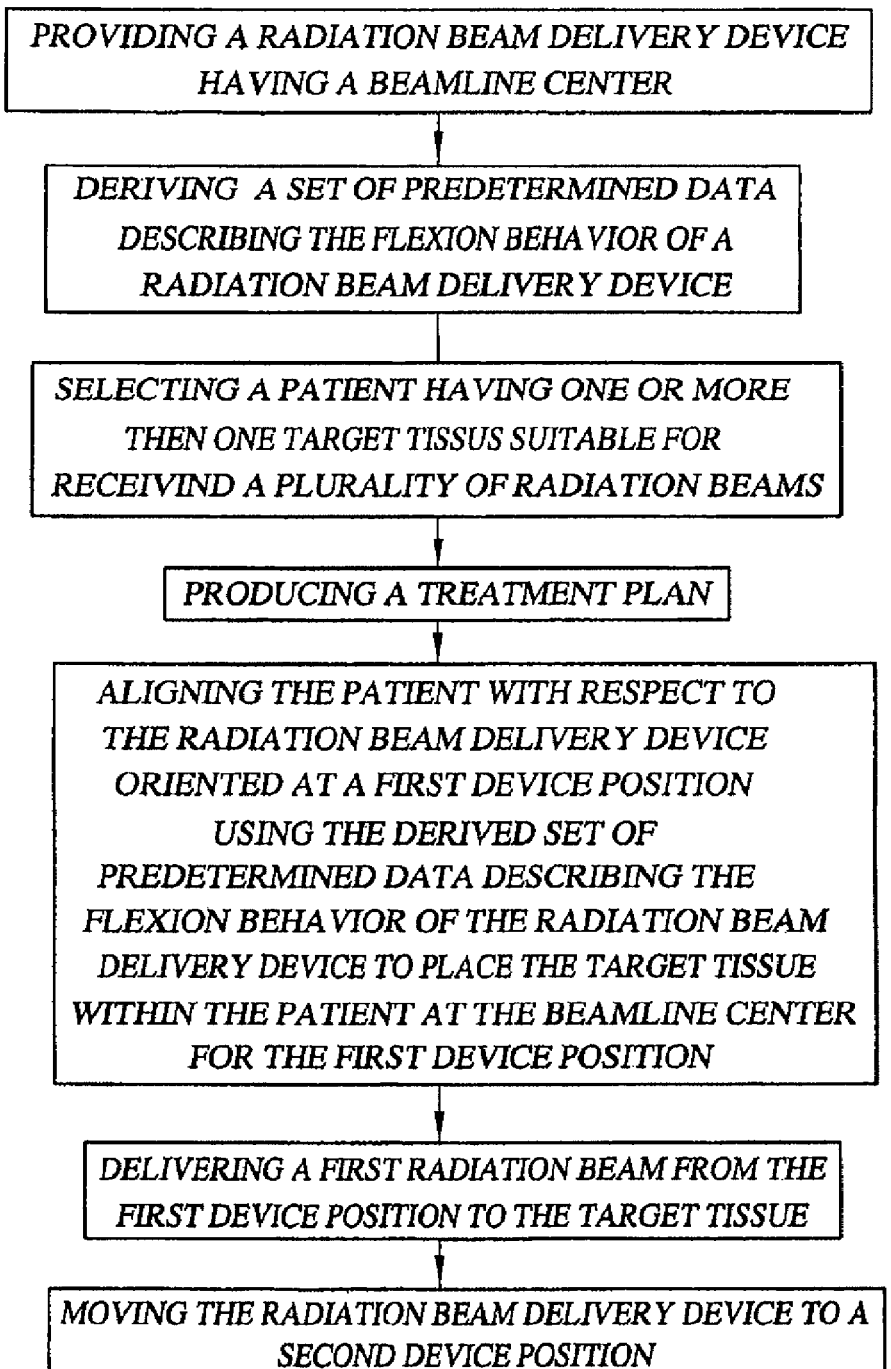

Referring now to FIG. 11 there is shown a lateral cutaway, schematic view of the device 10 illustrating an example of the components of the device 10 allowing for fine pitch movement. As can be seen, the components of the device 10 allowing for fine pitch movement comprise a linear actuator 82, a tabletop 74, a center of rotation for pitch angle 84, a lower center of rotation for the actuator 86, and an upper center of rotation for the actuator 88.

In another embodiment of the present invention, there is provided a method of aligning a patient for delivering a plurality of radiation beams, such as proton beams, from a radiation beam delivery device at a plurality of device positions. Referring now to FIG. 12, FIG. 13, FIG. 14 and FIG. 15, there are shown flow charts depicting some steps of various embodiments of the method of the present invention. The method comprises compensating for flexion of a radiation beam delivery device within a gantry during movement of the radiation beam delivery device from a first device position to a second device position by using a set of predetermined data describing the flexion behavior of the radiation beam delivery device so that the target tissue within the patient is placed at the beamline center for the radiation beam delivery device at the second device position. The method allows a patient to be irradiated from a plurality of delivery device positions without the patient undergoing a full realignment procedure between repositioning of the radiation beam delivery device from the first device position to the second device position. The method advantageously reduces the time and cost for delivering a plurality of radiation beams from a plurality of device positions.

The present method of aligning a patient for delivering a plurality of radiation beams from a plurality of device positions comprises the following steps. First, a set of data describing the flexion behavior of a radiation beam delivery device during repositioning is derived. Next, a suitable patient is selected, where the patient has one or more than one target tissue suitable for receiving a plurality of radiation beams. Then, a treatment plan is produced. Next, the patient is aligned with respect to a reference set-up position to place the target tissue within the patient at the isocenter. Then, the radiation beam delivery device is moved to a first device position. Next, flexion of the radiation beam delivery device produced by the move to the first device position is compensated for using the set of predetermined data describing the flexion behavior of the radiation beam delivery device to place the target tissue within the patient at the beamline center for the radiation beam delivery device at the first device position. Then, a first radiation beam from the radiation beam delivery device at the first device position is delivered to the target tissue within the patient. Next, the radiation beam delivery device is moved to a second device position. Then, flexion of the radiation beam delivery device produced by the move to the second device position is compensated for using the set of predetermined data describing the flexion behavior of the radiation beam delivery device to place the target tissue within the patient at the beamline center for the radiation beam delivery device at the second device position. Next, a second radiation beam from the radiation beam delivery device at the second device position is delivered to the target tissue within the patient.

Figure 16:
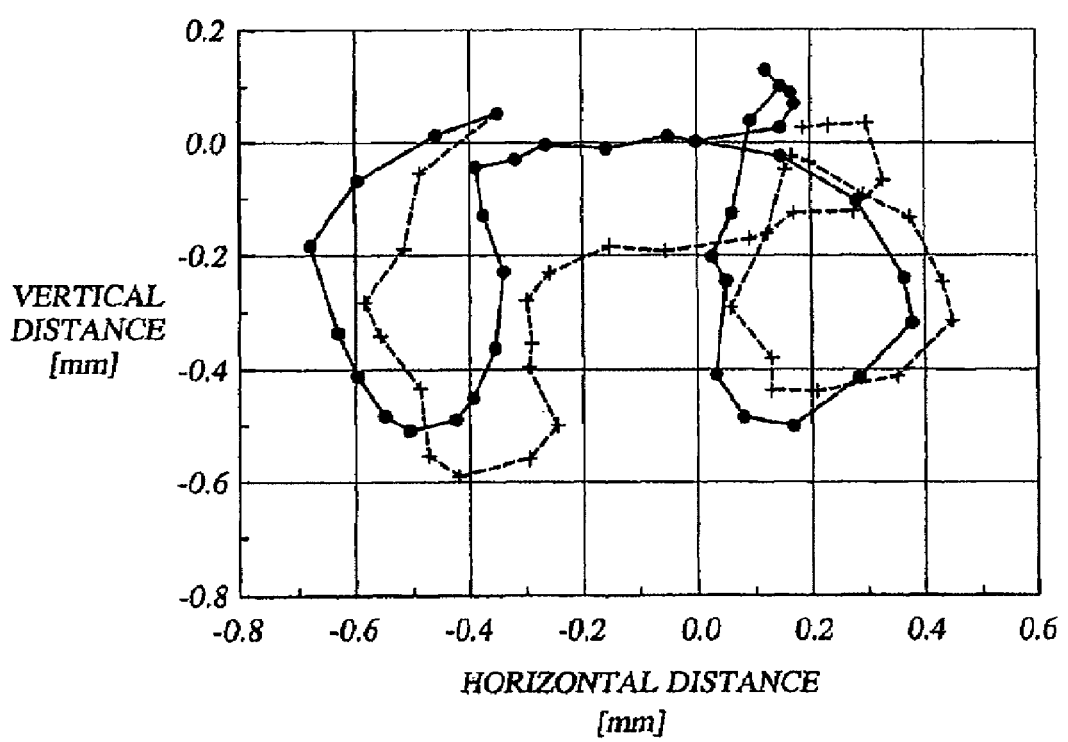
FIG. 16 and FIG. 17 are examples of plots of data sets describing the flexion behavior of a sample radiation beam delivery device in the plane of gantry rotation, and perpendicular to the plane of gantry rotation, respectively, that can be used with the method of alignment of the present invention.
Figure 17:
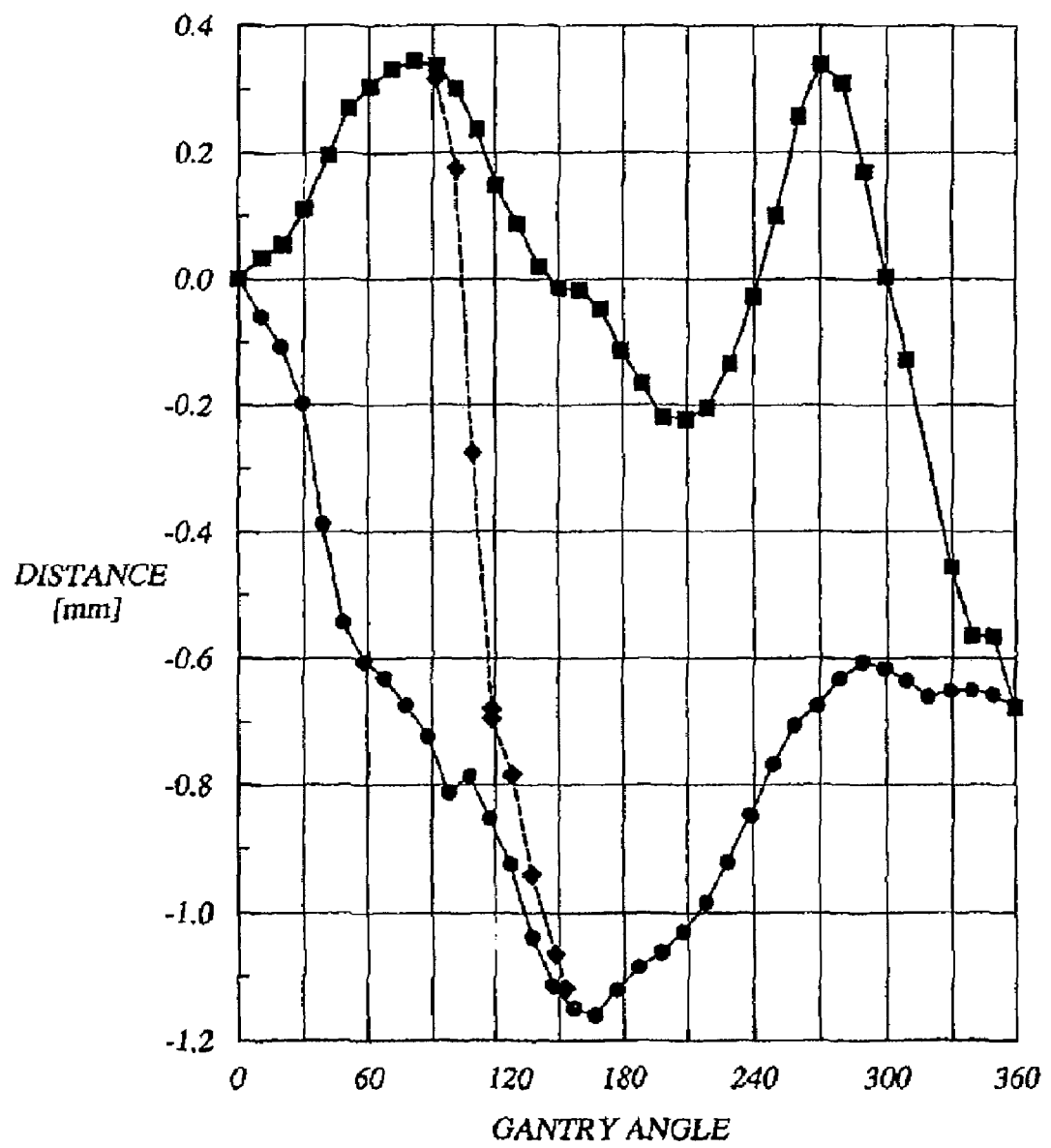

In one embodiment, the radiation beam delivery device is moved to a third device position. Then, flexion of the radiation beam delivery device produced by the move to the third device position is compensated for using the set of predetermined data describing the flexion behavior of a radiation beam delivery device derived previously. Next, a third radiation beam from the radiation beam delivery device at the third device position is delivered to the target tissue within the patient. As will be understood by those with skill in the art with reference to this disclosure, additional radiation beams from additional device positions can be delivered to the target tissue within the patient by compensating for flexion of the radiation beam delivery device produced by the move to the additional device positions using the set of predetermined data describing the flexion behavior of a radiation beam delivery device. Each of these steps will now be disclosed in greater detail. First, a set of data describing the flexion behavior of a radiation beam delivery device is derived. Referring now to FIG. 16 and FIG. 17, there are shown plots of combined data sets describing the flexion behavior of two sample radiation beam delivery devices at the Loma Linda University Proton Treatment Facility, Loma Linda, Calif., US, in the plane of gantry, rotation, FIG. 16, and perpendicular to the plane of gantry rotation, FIG. 17. The measurements were made as follows.

Measurement of the mechanical isocenter was divided into two perpendicular components. The first component was used to describe the radial deviation as the gantry rotates, while the second component describes the axial runout. The radial component was measured by first inserting a milled block into the end of the beam delivery device closest to where the patient would be located during a treatment. The milled block extended from the delivery device to beyond the estimated virtual center of the gantry. A theodolite with a 32× magnification telescope was placed in the room approximately three meters from the presumed isocenter and coaxially with it. A grid on the block was observed through the theodolite telescope while the gantry was rotated in increments of 10°. After each movement, the coordinate of the cross in the theodolite sight relative to the grid was recorded. After the data were measured, they were transformed from the gantry coordinate system to the room coordinate system and plotted. The axial runout was measured with a dial indicator that was rigidly affixed to the end of the patient positioner with its sensitive point touching the milled block at the previously determined radial isocenter. Again, the gantry was rotated in increments of 10°, stopping to record the measurements. Both radial and axial tests were performed in the clockwise and counterclockwise directions. Circles represent the path of the beamline center during a clockwise rotation while crosses represent the path of the beamline center during a counter clockwise rotation.

Next, a suitable patient is selected, where the patient has one or more than one target tissue suitable for receiving a plurality of radiation beams. A suitable patient will be one having one or more than one target tissue having a disease or condition amenable to teletherapy, such as a solid tissue neoplasm, an arterio-venous malformations or Parkinson's disease. In a preferred embodiment, the patient will have a solid tissue neoplasm susceptible to radiation therapy, such as a neoplasm selected from the group consisting of acoustic neuroma, adenocarcinoma, astrocytoma, chordoma, meningioma, nasopharyngeal carcinoma and pituitary adenoma.

Then, a treatment plan is produced using conventional methods. For example, the patient is registered and immobilized to a patient positioner of a scanner, such as an XCT scanner or other suitable device, using appropriate registration and immobilization procedures, and the patient is scanned. The information from the scan is then transferred to a treatment planning system, and the treatment plan is produced.

Next, the patient is aligned such that the target tissue within the patient is at the beamline center of the radiation beam delivery device for delivering a first beam of radiation to the target tissue. In one embodiment, the patient is aligned using a two-stage patient positioner device for aligning a patient for delivering a plurality of radiation beams according to the present invention. This can be accomplished, for example as follows.

Figure 18:
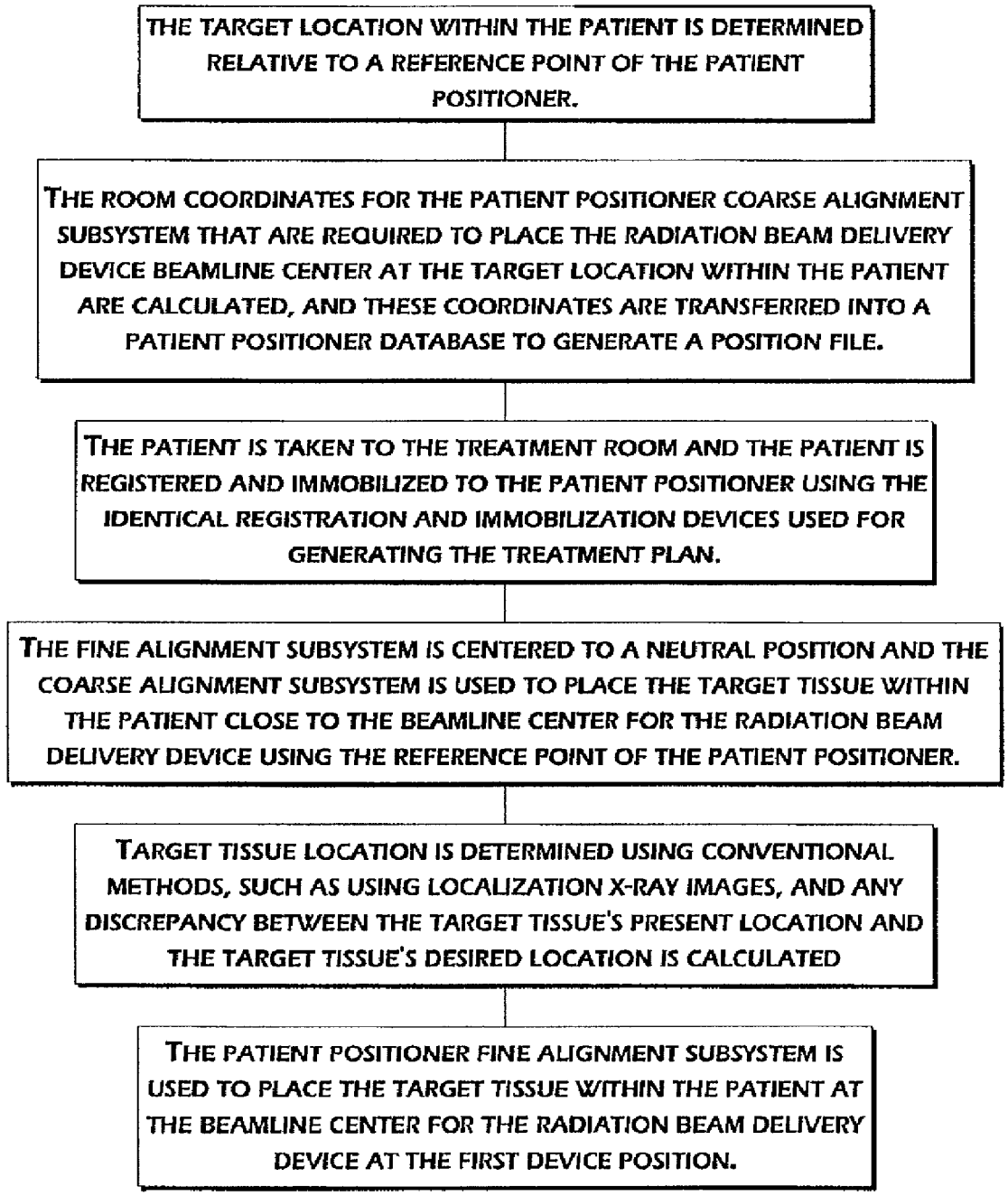
FIG. 18 is a flowchart illustrating one embodiment of a method of positioning a patient for receiving radiation treatment.

FIG. 18 is a flowchart illustrating one embodiment of a method of positioning a patient for receiving radiation treatment. First, the target location within the patient is determined relative to a reference point of the patient positioner. Then, the room coordinates for the patient positioner coarse alignment subsystem that are required to place the radiation beam delivery device beamline center at the target location within the patient are calculated, and these coordinates are transferred into a patient positioner database to generate a position file. Next, the patient is taken to the treatment room and the patient is registered and immobilized to the patient positioner using the identical registration and immobilization devices used for generating the treatment plan. Then, the fine alignment subsystem is centered to a neutral position and the coarse alignment subsystem is used to place the target tissue within the patient close to the beamline center for the radiation beam delivery device using the reference point of the patient positioner. Then, the target tissue location is determined using conventional methods, such as using localization x-ray images, and any discrepancy between the target tissue's present location and the target tissue's desired location is calculated. Next, the patient positioner fine alignment subsystem is used to place the target tissue within the patient at the beamline center for the radiation beam delivery device at the first device position.

In some embodiments, a method of aligning a patient for delivering multiple beams of radiation comprises the following steps. First, the patient is registered and immobilized to the patient positioner of an XCT scanner, or other suitable device, using an appropriate registration device and an appropriate immobilization device. Then, an XCT scan of the patient is performed. The XCT images are transferred to a treatment planning system and a treatment plan is developed.

Next, the target location for the isocenter within the patient is determined relative to a reference point of the patient positioner. Then, calculations are made of the room co-ordinates of the treatment gantry patient positioner base subsystem that are required to place the gantry isocenter at the target location within the patient. These co-ordinates are entered into a patient positioner database to generate a position file.

Then, the patient is taken to the treatment room. The gantry snout is preferably retracted to avoid a possible collision with the patient or equipment and the gantry is rotated to a beam delivery angle of 00. The patient is registered and immobilized to the patient positioner using the identical registration and immobilization devices used for performing the XCT scan.

Next, an operator commands the patient positioner to center the fine alignment subsystem using an automatic zeroing command. Then, the operator manually drives the patient positioner base sub-system to place the location of the target within the patient within a few centimeters of the virtual isocenter of the gantry. The orientation of the patient positioner at this time approximately matches the prescribed orientation.

Next, the patient's position file that was previously generated is loaded and the operator commands the patient positioner base sub-system to "go to" the loaded position, thereby placing the target within the patient within a few millimeters of the virtual isocenter. The operator then commands the patient positioner base sub-system to move to the next radiation field, either by "turn wheels for yaw" or "turn wheels to isocenter" as needed.

Then, a localization image, such as an x-ray, is taken with either an electronic imaging device or film. The gantry is rotated to 900 and another localization image is taken orthogonally to the first localization image.

Next, a patient alignment algorithm uses the two localization images to compute the discrepancy between the patient's current location and orientation and the prescribed location and orientation. The therapist verifies the miss-alignment and suggested move and activates an enable switch on the patient positioner. The patient positioner fine alignment sub-system automatically rotates and translates the patient to correct for the difference in location and orientation.

After the initial miss-alignment has been corrected, the therapist commands the patient positioner to "set reference isocenter." This command determines the gantry arrival direction and queries sensors that measure the gantry rotation angle, snout extension, snout delta (skewness), and all patient positioner positions. Then, the aperture and bolus for the field are installed into the snout, the gantry rotated to the treatment angle, and the snout extended to its treatment position.

The operator then commands the patient positioner fine alignment sub-system to "compensate isocenter." This command queries the gantry rotation angle, gantry arrival direction, snout extension, snout delta, and all patient positioner positions. The system then automatically compares the projection of the beam central axis at the reference gantry angle and the current gantry angle based on pre-measured data sets. Referring now to FIG. 1 and FIG. 2, there are shown plots of pre-measured data sets in the plane of gantry rotation and perpendicular to the plane of rotation. The system then calculates the required move of the fine alignment subsystem of the positioner to compensate for the difference.

The therapist activates the enable switch and the fine alignment subsystem automatically translates the patient in all three directions to compensate for the gantry sag, gantry arrival direction, snout sag, and snout skewness. Then, the operator delivers the treatment beam. The snout is retracted and the gantry rotated to 900 The steps disclosed in this paragraph are then repeated for each additional treatment field until the treatment has been completed.

After the patient is aligned, a first radiation beam from the first device position is delivered to the target tissue within the patient. Next, the radiation beam delivery device is moved to a second device position. Then, flexion of the radiation beam delivery device produced by the move to the second device position is compensated for using the set of predetermined data describing the flexion behavior of the radiation beam delivery device so that the target tissue within the patient is placed at the beamline center for the radiation beam delivery device at the second device position. In a preferred embodiment, compensation is accomplished by moving the patient and patient positioner as a unit, such as by using a two-stage patient positioner device according to the present invention. In another preferred embodiment, compensation is accomplished by one or more than one action selected from the group consisting of shifting an aperture or block holding cone with respect to the center of the beam delivery apparatus, shifting the position of the defining collimators of the beam delivery apparatus (such as the leaves of a multi-leaf collimator), and offsetting the scan pattern of a magnetically scanned beam, where each of these actions can be combined with rotation of the gantry as necessary to maintain the direction and the aiming point of the beam, as will be understood by those with skill in the art with reference to this disclosure. Next, a second radiation beam from the second device position is delivered to the target tissue within the patient.

The present method can also be used with other therapy delivery techniques, including serial (fan beam) tomotherapy, spiral (helical) tomotherapy, intensity modulated arc therapy (IMAT), cone beam dynamic therapy (sliding window), or cone beam segmental therapy (step and shoot), as well as being used for diagnostic radiation exposures, as will be understood by those with skill in the art with reference to this disclosure.

Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. A method for improving radiation therapy by reducing patient alignment time, decreasing cost per patient, and reducing non-therapeutic radiation exposure to a patient, the method comprising:
   providing a computerized treatment planning system;
   providing an isocentric mechanical gantry that houses a beam delivery system for radiation therapy, the gantry having a gantry rotation axis;
   performing a single alignment procedure by reproducibly interfacing a patient with radiation equipment to obtain anatomical and morphological information, the alignment procedure comprising each of the following five steps:
      registering the patient by placing the patient on a patient positioner in a reproducible manner, the patient positioner configured to rotate about at least one patient positioner rotation axis;
      immobilizing the patient by attaching the registered patient to the patient positioner so that the patient and patient positioner move together as a single unit in a controlled fashion;
      localizing target tissue within the patient by determining the location of the target relative to radiation equipment;
      positioning the patient by moving the patient positioner to place the target in a desired orientation at a desired location, both with respect to the radiation equipment;
      verifying the target's orientation and location with respect to the radiation equipment using the same technique used in the localizing step;
   with the treatment planning system, using the results of the single alignment procedure to create a single set of pre-measured data representing a fine positional adjustment that compensates for characteristics of the patient and patient positioner together;
   using the single set of pre-measured data to accurately position the patient with respect to the gantry; and
   irradiating the patient from multiple gantry directions without realignment, each time relying on the same single set of pre-measured data resulting from the single alignment procedure.

2. The method of claim 1, further comprising providing pre-measured data sets characterizing gantry-specific movement and using those data sets to compensate for that movement before irradiating the patient.

3. The method of claim 1, further comprising, before irradiating the patient, using a fine alignment sub-system to move the patient and patient positioner with respect to the gantry to compensate for positional inaccuracies resulting from gantry movement.

4. The method of claim 1, further comprising, before irradiating the patient, adjusting the gantry, shifting an aperture or block holding cone, shifting the position of collimators, or shifting the magnetic scan pattern to compensate for deflection of the gantry structure.

5. The method of claim 1, wherein the patient positioner is a movable table.

6. The method of claim 1, wherein placing the patient on a patient positioner comprises placing the patient in a supine position.

7. The method of claim 1, wherein registering the patient further comprises at least partially surrounding the patient with low-density foam.

8. The method of claim 1, wherein immobilizing the patient is accomplished with a thermoplastic net.

9. The method of claim 8, wherein the thermoplastic net covers the patient and registration device and attaches to the patient positioner.

10. The method of claim 1, further comprising performing high precision localization and verification using radiography to find fiducial markers.

11. The method of claim 1, further comprising aligning the gantry rotation axis and the patient positioner rotation axis such that the two axes intersect at an isocenter.

12. The method of claim 1, wherein performing a single alignment procedure and using the single set of pre-measured data positions the target at the isocenter.

13. A method for improving teletherapy by reducing patient alignment time, decreasing cost per patient, and reducing radiation exposure to a patient, the method comprising:
   providing a computerized treatment planning system;
   providing a gantry for delivering radiation;
   performing a single alignment procedure to create a single set of pre-measured data that is specific to the patient and to the gantry;
   using the single set of pre-measured data and the treatment planning system and a fine alignment subsystem to precisely position the patient; and
   irradiating a patient from multiple gantry directions without realigning the patient between radiation doses.

14. A system for aligning a patient for delivering multiple beams of radiation, the system comprising:
   a registration and immobilization device configured to register and immobilize a patient to a diagnostic positioner;
   a scanner configured to perform a scan of the patient to create images and provide the images to a computerized treatment planning system;
   the computerized treatment planning system configured to use the images to determine a target location in the patient that is desired to correspond to an isocenter of a radiation treatment device having a gantry and to determine the target location relative to a reference point of the diagnostic positioner;
   a calculating device configured to calculate, based on known differences between the diagnostic positioner and a treatment positioner and on the relationship between the treatment positioner and the radiation treatment device, coordinates for placing the target location at the isocenter of the radiation treatment device;
   the treatment positioner configured to accept the same registration and immobilization devices that were used for the scan;
   an automatic positioner configured to use the coordinates to automatically position the target at or near the isocenter;
   an imager configured to acquire one or more localization images with the patient in one or more radiation fields for determination of any discrepancy between the actual position of the target and the actual isocenter;
   a fine alignment subsystem configured to automatically correct for the discrepancy, if any; and
   the automatic positioner configured to automatically compensate for movement of the gantry and movement of a snout of the radiation treatment device, the compensation based on:
      pre-measured data sets that recorded movement of the radiation treatment device during gantry rotation and snout extension; and
      sensors recording the present gantry angle and snout extension.

15. The system of claim 14, wherein: the automatic positioner is further configured to use the fine alignment subsystem to automatically position the target at or near the isocenter.

16. The system of claim 14, wherein: the automatic positioner is further configured to use the fine alignment subsystem to automatically compensate for movement of the gantry and movement of a snout of the radiation treatment device.

17. The system of claim 14, wherein the same fine alignment subsystem is configured to accomplish each of the following:

use the coordinates to automatically position the target at or near the isocenter;
automatically correct for any discrepancy between the actual position of the target and the actual isocenter determined by one or more localization image(s); and
automatically compensate for movement of the gantry and movement of the snout.

* * * * *

UNITED STATES PATENT AND TRADEMARK OFFICE
CERTIFICATE OF CORRECTION

| | | |
|---|---|---|
| PATENT NO. | : 8,083,408 B2 | Page 1 of 1 |
| APPLICATION NO. | : 12/877019 | |
| DATED | : December 27, 2011 | |
| INVENTOR(S) | : Michael F. Moyers | |

It is certified that error appears in the above-identified patent and that said Letters Patent is hereby corrected as shown below:

In The Drawings:

On Sheet 15 of 19 (Box No. 3) (Fig. 15), please change "THEN" to --THAN--.

On Sheet 15 of 19 (Box No. 3) (Fig. 15), please change "TISSUS" to --TISSUE--.

On Sheet 15 of 19 (Box No. 3) (Fig. 15), please change "RECEIVIND" to --RECEIVING--.

On Sheet 16 of 19 (Box No. 3) (Fig. 15) (CONTINUED), please change "MOVINGTHE" to --MOVING THE--.

On Sheet 19 of 19 (Box No. 5) (Fig. 18), after "CALCULATED" please insert --.--.

On Column 2, Line 27, after "tissues" please insert --.--.

On Column 3, Line 37 (Approx.), please change "Further, It" to --Further, it--.

On Column 5, Line 67, please change "disclosure" to --invention;--.

On Column 14, Line 25, please change "900" to --900.--.

Signed and Sealed this

Twenty-third Day of October, 2012

David J. Kappos
*Director of the United States Patent and Trademark Office*